US007932047B2

(12) United States Patent
Ridder et al.

(10) Patent No.: US 7,932,047 B2
(45) Date of Patent: *Apr. 26, 2011

(54) METHOD FOR DETECTING NEOPLASTIC DISORDERS IN A SOLUBILIZED BODY SAMPLE

(75) Inventors: Ruediger Ridder, Schriesheim (DE); Anja Reichert, Nussloch (DE); Magnus Von Knebel Doeberitz, Heidelberg (DE); Matthias Herkert, Heidelberg (DE); Alexander Duwe, Heidelberg (DE); Rainer Hipfel, Balingen (DE); Peter Martin, Gaiberg (DE)

(73) Assignee: MTM Laboratories, AG, Heidelberg (DE)

(*) Notice: Subject to any disclaimer, the term of this patent is extended or adjusted under 35 U.S.C. 154(b) by 1192 days.

This patent is subject to a terminal disclaimer.

(21) Appl. No.: 10/569,758

(22) PCT Filed: Aug. 20, 2004

(86) PCT No.: PCT/EP2004/051872
§ 371 (c)(1),
(2), (4) Date: Aug. 1, 2006

(87) PCT Pub. No.: WO2005/088311
PCT Pub. Date: Sep. 22, 2005

(65) Prior Publication Data
US 2007/0190529 A1  Aug. 16, 2007

(30) Foreign Application Priority Data
Aug. 25, 2003  (EP) ..................... 03103218

(51) Int. Cl.
C12Q 1/00 (2006.01)
G01N 1/00 (2006.01)
G01N 21/00 (2006.01)
G01N 21/75 (2006.01)
G01N 21/76 (2006.01)
G01N 33/00 (2006.01)
G01N 33/48 (2006.01)
G01N 33/53 (2006.01)
G01N 33/566 (2006.01)
G01N 33/567 (2006.01)
G01N 33/574 (2006.01)
C12P 21/08 (2006.01)

(52) U.S. Cl. ............ 435/7.23; 435/4; 435/7.1; 435/7.21; 435/7.92; 436/63; 436/64; 436/164; 436/166; 436/172; 436/174; 436/501; 530/350; 530/386; 530/387.1; 530/387.3; 530/388.2

(58) Field of Classification Search .................. None
See application file for complete search history.

(56) References Cited

U.S. PATENT DOCUMENTS

| 4,281,061 | A | 7/1981 | Zuk et al. |
|---|---|---|---|
| 5,489,537 | A | 2/1996 | Van Aken |
| 5,624,819 | A | 4/1997 | Skolnick et al. |
| 5,739,027 | A | 4/1998 | Kamb |
| 5,801,236 | A | 9/1998 | Kamb |
| 5,889,169 | A | 3/1999 | Beach et al. |
| 5,976,799 | A | 11/1999 | O'Brien et al. |
| 5,989,815 | A | 11/1999 | Skolnick et al. |
| 5,994,095 | A | 11/1999 | Kamb |
| 6,033,847 | A | 3/2000 | Sherr et al. |
| 6,037,462 | A | 3/2000 | Kamb |
| 6,060,301 | A | 5/2000 | Kamb |
| 6,090,579 | A | 7/2000 | Albone et al. |
| 6,140,473 | A | 10/2000 | Kamb |
| 6,180,776 | B1 | 1/2001 | Kamb |
| 6,210,949 | B1 | 4/2001 | Stone et al. |
| 6,218,146 | B1 | 4/2001 | Kamb |
| 6,277,579 | B1 | 8/2001 | Lazar et al. |
| 6,316,208 | B1 | 11/2001 | Roberts et al. |
| 6,355,424 | B1 | 3/2002 | Lorincz et al. |
| 6,403,383 | B1 | 6/2002 | Casterlin et al. |
| 6,576,420 | B1 | 6/2003 | Carson et al. |
| 6,686,151 | B1 | 2/2004 | Lazar et al. |
| 6,709,832 | B1 | 3/2004 | Von Knebel Doeberitz et al. |
| 7,306,926 | B2 | 12/2007 | Doeberitz et al. |
| 7,517,662 | B2 | 4/2009 | Ridder et al. |
| 2001/0039023 | A1 | 11/2001 | Schubert |
| 2001/0051364 | A1 | 12/2001 | Michon et al. |
| 2002/0086288 | A1 | 7/2002 | Bird et al. |
| 2002/0106685 | A1 | 8/2002 | Henning et al. |

(Continued)

FOREIGN PATENT DOCUMENTS

EP  0643836 A1  3/1995

(Continued)

OTHER PUBLICATIONS

He, et al., "Expression, Deletion and Mutation of p16 Gene in Human Gastric Cancer" *World J. of Gastroenterology* 7(4): 515-521 (2001).
Myung, et al., "Loss of p16 and p27 Is Associated With Progression of Human Gastric Cancer" *Cancer Letters* 153:129-136 (2000).
Nakao et al., "Induction of p16 During Immortalization HPV 16 and 18 and Not During Malignant Transformation" *British J of Cancer* 75(10):1410-1416, 1997.
O'Nions, et al., "p73 Is Over-Expressed in Vulval Cancer Principally As the Δ2 Isoform" *British J. Cancer* 85(10):1551-1556 (Nov. 2001).
Sano, et al., "Overexpression of P16 and P14ARF Is Associated With Human Papillomavirus Infection in Cervical Squamous Cell Carcinoma and Dysplasia" *Pathology Int.* 52:375-383 (May 2002).

(Continued)

Primary Examiner — Alana M. Harris
(74) Attorney, Agent, or Firm — Perkins Coie LLP; Viola T. Kung

(57) ABSTRACT

The present invention relates to a method for the early diagnosis of neoplastic disorders such as cancers as well as their precursor stages, particularly cancers of the respiratory tract, the urinary system, the reproductive tract, cancer associated with HPV infection or cancer of the anogenital tract, from solubilized body samples. The invention is also directed to test kits usable for this purpose as well as in-vitro diagnostic devices. The development of the kits and in-vitro diagnostic devices for the above purpose is also one aspect of the present invention.

35 Claims, 1 Drawing Sheet

U.S. PATENT DOCUMENTS

| | | |
|---|---|---|
| 2002/0127545 A1 | 9/2002 | Lorincz et al. |
| 2003/0091992 A1 | 5/2003 | Lorincz et al. |
| 2003/0157482 A1 | 8/2003 | Keesee et al. |
| 2003/0175768 A1 | 9/2003 | Carson et al. |
| 2004/0023288 A1* | 2/2004 | Ridder et al. ............ 435/6 |
| 2004/0180362 A1 | 9/2004 | Lazar et al. |
| 2004/0180388 A1 | 9/2004 | Von Knebel Doeberitz et al. |
| 2004/0202996 A1 | 10/2004 | Williams et al. |
| 2005/0084858 A1 | 4/2005 | Wasielewski et al. |
| 2005/0118568 A1 | 6/2005 | Karlsen |

FOREIGN PATENT DOCUMENTS

| | | |
|---|---|---|
| EP | 0723156 A | 7/1996 |
| EP | 1038022 A2 | 9/2000 |
| EP | 1038029 A2 | 9/2000 |
| EP | 1217377 A2 | 6/2002 |
| EP | 1230396 A2 | 8/2002 |
| EP | 1305631 A1 | 5/2003 |
| EP | 1333278 A1 | 8/2003 |
| EP | 1388734 A1 | 2/2004 |
| EP | 1463839 A2 | 10/2004 |
| EP | 1470419 A1 | 10/2004 |
| EP | 1525476 A1 | 4/2005 |
| WO | WO 9220796 A2 | 11/1992 |
| WO | WO 93/12426 A1 | 6/1993 |
| WO | WO 9904238 | 1/1999 |
| WO | WO 99/29890 A2 | 6/1999 |
| WO | WO 99/31273 A2 | 6/1999 |
| WO | WO 00/31538 A1 | 6/2000 |
| WO | WO 01/36681 A2 | 5/2001 |
| WO | WO 02/08764 A1 | 1/2002 |
| WO | WO 03/057914 A | 7/2003 |
| WO | WO 03/065035 A1 | 8/2003 |
| WO | WO 2004/013632 A | 2/2004 |
| WO | WO 2004/092734 A2 | 10/2004 |

OTHER PUBLICATIONS

Sano et al., "Expression Status of p16 Protein Is Associated With Human Papillomavirus Oncogenic Potential in Cervical and Genital lesions" *American J. Pathology* 153(6)1741,1998.

Sherr, "The Ink4a/Arf Network in Tumor Suppression" *Nature Reviews Mol. Cell Bio* 2:731-737, (2001).

Takeuchi, et al., "Altered p16/MTSi/CDKN2 and Cycling D1/PRAD-1 Gene Expression Is Associated With the Prognosis of Squamous Cell Carcinoma of the Esophagus" *Clinical Cancer Research* 3:2229-2236, (1997).

Tsujie, et al., "Expression of Tumor Suppressor Gene p16INK4 Products in Primary Gastric Cancer" *Oncology* 58:126-136 (2000).

Castle Philip E et al: "Stability of archived liquid-based cervical cytologic specimens", Cancer, vol. 99, No. 2, Apr. 25, 2003, p. 89-96, XP002331364.

Klaes R et al: "Overexpression of p16INK4a as a specific marker for dysplastic and neoplastic epithelial cells of the cervix uteri", Int. Journal of Cancer, New York, vol. 92, No. 2, 2001, p. 276-284, XP002225497.

Brule Van Den A J C et al: "Rapid detection of human papillomavirus in cervical scrapes by combined general primer-mediated and type-specific polymerase chain reaction", Journal of Clinical Microbiology, Washington DC, vol. 28, No. 12, 1990-12, p. 2739-2743, abstract p. 2739, col. 2, line 5—p. 2741, col. 1, line 4, XP009015539.

Agoff, S. Nicholas, M.D., et al., p16$^{INK4a}$ "Expression Correlates with Degree of Cervical Neoplasia: A Comparison with ki-67 Expression and Detection of High-Risk HPV Types", The United States and Canadian Academy of Pathology, Inc., vol. 16, No. 7, pp. 665-673 (2003).

Aho et al. (J. Cell Sci. Apr. 1, 2002; 115 (Pt 7): 1391-1402).

Betticher, et al., "Prognostic significance of CCND1 (cyclin D1) overexpression in primary resected non-small-cell lung cancer", British J. of Cancer 73: 294-300 (1996).

Bhakdi, Sucharit (J. Biochem. Biophys. Methods. Jan.-Feb. 2, 1980; 2 (1): 79-90).

Bibbo et al. (Acta Cytologica. Jan.-Feb. 2002; 46 (1): 25-29).

Browne, et al., "Analysis of the L1 Gene Product of Human Papillomavirus Type 16 by Expression in a Vaccinia Virus Recombinant", J. gen. Virol., 69: 1263-73 (1988).

Carayol, et al., "NK cells differentiated from bone marrow, cord blood and peripheral blood stem cells exhibit similar phenotype and functions", Eur. J. Immunol. 28: 1991-2002 (1998).

Castellano et al. Cancer Res. Nov. 1, 1997; 57: 4868-75.

Cattoretti, et al., "Monoclonal antibodies against recombinant parts of the Ki-67 antigen (MIB 1 and MIB 3) detect proliferating cells in microwave-processed formalin-fixed paraffin sections", Journal of Pathology, 168: 357-363 (1992).

Chilton, et al., "Estrogen Regulation of the Central Enzymes Involved in O- and N-Linked Glycoprotein Assembly in the Developing and the Adult Rabbit Endocervix", Endocrinology, 123(3): 1237-44 (1988).

Dai et al. Gastroenterology. 2000; 119: 929-42.

Davey et al. (Arch. Pathol. Lab. Med. Feb. 2000, vol. 124, pp. 203-211).

Day et al. (Am J Clin Pathol. 2002; 118: 41-46).

De Boer, et al., "Changing Roles of Cadherins and Catenins during Progression of Squamous Intraepithelial Lesions in the Uterine Cervix", American Journal of Pathology, 155(2): 505-515 (1999).

Di Loreto et al., "Different binding to squamous and columnar epithelium of the uterine cervix as a marker of epithelial differentiation", Bas. Appl. Histochem. 31: 143-52 (1987).

Dimitriadis, Giorgos J. (Anal. Biochem. Oct. 1, 1979; 98 (2): 445-451).

Epenetos, et al., "Use of Two Epithelium-Specific Monoclonal Antibodies for Diagnosis of Malignancy in Serous Effusions", The Lancet, 1004-6 (Nov. 6, 1982).

Geradts et al. (Am. J. Pathol. Jun. 1999; 154 (6): 1665-1671).

Geradts, et al., "Immunohistochemical Detection of the Cyclin-dependent Kinase Inhibitor 2/Multiple Tumor Suppressor Gene 1 (CDKN2/MTS1) Product p16INK4A in Archival Human Solid Tumors: Correlation with Retinoblastoma Protein Expression", Cancer Research 55: 6006-11 (Dec. 15, 1995).

Grundhoefer, et al., "Determination of Liquid-Based Cervical Cytology Specimen Adequacy Using Cellular Light Scatter and Flow Cytometry", Cytometry (Communications in Clinical Cytometry), 46: 340-4 (Dec. 15, 2001).

Guillou, et al., "Squamous Cell Carcinoa of the Lung in a Nonsmoking, Monirradiated Patient with Juvenile Laryngotracheal Papillomatosis", The American Journal of Surgical Pathology, 15(9) 891-8 (1991).

Gump et al. J. Biol. Chem. Feb. 28, 2003; 278 (9): 6619-22.

Hamid, et al., "Detection of Human Probombesin mRNA in Neuroendocrine (Small Cell) Carcinoma of the Lung", Cancer, 63:266-71 (1989).

Harada, et al., "Phenotypic Difference of Normal Plasma Cells from Mature Myeloma Cells", Blood, 81(10): 2658-63 (1993).

Heid, et al., "Cell type-specific desmosomal plaque proteins of the plakoglobin family: plakophilin 1 (band 6 protein)", Differentiation, 58: 113-31 (1994).

Hermann, et al., "Reduced LAK Cytotoxicity of Peripheral Blood Mononuclear Cells in Patients with Bladder Cancer: Decreased LAK Cytotoxicity Caused by a Low Incidence of CD56+ and CD57+ Mononuclear Blood Cells", Journal of Clinical Immunology, vol. 10, No. 6, pp. 311-320 (1990).

Hirama, et al., "p. 16 (CDKN2/Cylin-dependent Kinase-+ inhibitor/Multiple Tumor Suppressor-1) Gene Is Not Altered in Uterine Cervical Carcinomas or Cell Lines", *Modern Pathology*, 9(1) 26-31 (1996).

Iftner, et al., "Involvement of Human Papillomavirus Type 8 Genes E6 and E7 in Transformation and Replication", Journal of Virology, 62(10): 3655-61 (1988).

Ikeda et al. (J. Histochem. Cytochem. 1998; 46 (3): 397-403).

Jones, et al., Detection of T and B Cells in Many Animal Species Using Cross-Reactive Anti-Peptide Antibodies. The Journal of Immunology, 150: 5429-35 (1993).

Kelley, et al., "CDKN2 in HPV-Positive and HPV-Negative Cervical-Carcinoma Cell Lines", *Int. J. Cancer*, 63: 226-30 (1995).

Khleif et al. (Proc. Natl. Acad. Sci. USA. Apr. 1996 93: 4350-4354).

Kim, et al., "Absence of p. 15$^{INK4B}$ and p. 16$^{LINK4A}$ Gene Alterations in Primary Cervical Carcinoma Tissues and Cell Lines with Human Papillomavirus Infection", *Gynecologic Oncology*, 70: 75-9 (1998).

Kim, et al., "Underexpression of Cyclin-Dependent Kinase (CDK) Inhibitors in Cervical Carcinoma", Gynecologic Oncology, 71: 38-45 (1998).
Kimmig et al. (J. Cancer Res. Clin. Oncol. 1995; 121: 107-114).
von Knebel Doebertiz. (Disease Markers. (2001) 17 (3), pp. 123-128).
Koch, et al., "Specificity of antibodies to the purified Con A acceptor glycoproteins of cultured tumour cells", Br. J. Cancer, 53: 13-22 (1986).
Kommoss, et al., Inhibin-.sub..alpha.. CD99, HEA125, PLAP, and Chromogranin Immunoreactivity in Testicular Neoplasms and the Androgen Insensitivity Syndrome, Human Pathology, 31(9): 1055-61 (2000).
Larsson, et al., Tissue Plasminogen Activator and Urokinase in Normal, Dysplastic and Cancerous Squamous Epithelium of the Uterine Cervix, Thrombosis and Haemostasis, 58(3): 822-6 (1987).
Latza, et al., "Ber-EP4: new monoclonal antibody which distinguishes epithelia from mesothelia", J. Clin Pathol, 43: 213-9 (1990).
Levy et al. (differentiation. Dec. 1988; 39 (3): 185-196).
Liggett et al. (J. Clin. Oncol. Mar. 1998; 16 (3): 1197-1206).
Litvinov SV et al. American Journal of Pathology 148(3): 865-875, 1996.
Mao et al. Int. J. Cancer. 2007; 120: 2435-8.
Martens et al. (Cancer Cytopathology, Apr. 25, 1999; 87(2): 87-92).
Mason, et al., "Rapid Communication", American Journal of Pathology, 136(6) 1215-22 (Jun. 1990).
McCabe et al. (J. Immunol. Methods. Apr. 6, 1988; 108 (1-2): 129-135).
Milde-Langosch, et al., "P16/MTS1 and *p*RB expression in endometrial carcinomas", *Virchows Arch*, 434: 23-8 (1999).
Milde-Langosch, et al., "p. 16/*MTS1* Inactivation in Ovarian Carcinomas: High Frequency of Reduced Protein expression Associated with Hyper-Methylation or Mutation in Endometroid and Mucinous Tumors", *Int. J. Cancer*, 79: 61-5 (1998).
Mistretta, et al., "Isolation of a Carcino-Embryonic-Antigen (CEA) from a Liver Metastasis of Primary Adenocarcinoma of the Colon and Preparation of the Specific Antiserum", Specialia, 1209-10 (1974).
Mujica van Herckenrode, et al., Antibodies specific for HeLa glycoprotein antigens are also specific for human endocervical epithelium, Br. J. Cancer, (1988) 57, pp. 293-294.
Nair, et al., "Involucrin and Tumor Progression in the Uterine Cervix", Pathobiology, 64: 333-8 (1996).
Nuovo, et al., "In situ detection of the hypermethylation-induced inactivation of the p. 16 gene as a early event in oncogenesis", *PNAS*, 96(22): 12754-9 (Oct. 26, 1999).
Pagani, et al., "Expression of the Gastrin-Releasing Peptide Gene in Carcinomas of the Breast", Int. J. Cancer 47: 371-5 (1991).
Plath et al. J. Cell Biol. Sep. 18, 2000; 150 (6): 1467-77.
Qualtiere et al. (J. Immunol. Nov. 1977; 119(5): 1645-1651).
Ranki M. et al. Journal of Clinical Microbiology 28(9): 2076-2081, 1990.

Rogers, et al., "A Monoclonal Antibody Against a CEA-related Antigen Expressed on HT29 Colon Tumour Cells*", J. Cancer Clinic. Oncology, 20(10): 1279-86 (1981).
Ryder et al. (Clin. Chem. Dec. 1988 34 (12): 2513-2516).
Sano, et al., "Immunohistochemical overexpression of p.16 protein associated with intact retinoblastoma protein expression in cervical cancer and cervical intraepithelial neoplasia", *Pathology International*, 48: 580-5 (1998).
Serrano, et al., "A new regulatory motif in cell-cycle control causing specific inhibition of cyclin D/CDK4", *Nature*, 366: 704-7 (Dec. 16, 1993).
Shigemasa, et at, "p16 Overexpression: A Potential Early Indicator of Transformation in Ovarian Carcinoma", J. Soc. Gynecol Invest., 4(2): 95-102 (1997).
Shim, et al., "Profiling of Differentially Expressed Genes in Human Primary Cervical Cancer by Complementary DNA Expression Array", Clinical Cancer Research, 4: 3045-50 (1998).
Smedts, et al., "Changing Patterns of Keratin Expression During Progression of Cervical Intraepithelial Neoplasia", American Journal of Pathology, 136(3): 657-68 (Mar. 1990).
Smith, et al., "Cytochemical Demostration of Oxidative Damage in Alzheimer Disease by Immunochemical Enhancement of the Carbonyl Reaction with 2,4-Dinitrophenylhydrazine", The J. of Histochemistry & Cytochemistry, 46(6): 731-5 (1998).
Southern, et al., "Loss of Cytokeratin 14 Expression Is Related to Human Papillomavirus Type and Lesion Grade in Squamous Intraepithelial Lesions of the Cervix", Human Pathology, 32(12): 1351-5 (2001).
Suneja et al. Brain Res. Protocols. 1998; 3: 88-93.
Tam, et al., "Differential Expression and Cell Cycle Regulation of the Cyclin-dependent Kinase 4 Inhibitor p16INK4", Cancer Research, 54: 1816-20 (1994).
Tashiro, et al., "Immunohistochemical Study of Mucin Carbohydrates and Core Proteins in Human Ovarian Tumors", Human Pathology, 25(4): 364-72 (1994).
van der Poel, et al., "Can biological marker replace cyctoscopy? An update", Current Opinion in Urology, 11:503-9 (2001).
Versura, "Detection of mucus glycoconjugates in human cervical epithelium by lectin-colloidal gold technique in transmission electron microscopy", Bas. Appl. Histochem., 32: 219-27 (1998).
Waseem, et al., "Monoclonal antibody analysis of the proliferating cell nuclear antigen (PCNA)—Structural conservation and the detection of a nucleolar form", J. of Cell. Science, 96: 121-9 (1990).
Wentzensen et al. Cancer. 2006; 107: 2307-13.
Wong, et al., "Methylation of p16INK4A in primary gynecologic malignancy", Cancer Letters, 136: 231-5 (1999).
Wong, et al., p16INK4 and p15INK4B Alterations in Primary Gynecologic Malignancy, Gynecologic Oncology 5: 319-24 (1997).
Zimmer, et al., "Proliferating Cell Nuclear Antigen (PCNA) in Atypical and Malignant Meningiomas", Path. Res. Pract. 188: 951-8 (1992).

* cited by examiner

SEQUENCE LISTING

<160> NUMBER OF SEQ ID NOS: 25

<210> SEQ ID NO 1
<211> LENGTH: 20
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(20)
<223> OTHER INFORMATION:

<400> SEQUENCE: 1
cgaatagtta cggtcggagg                                          20

<210> SEQ ID NO 2
<211> LENGTH: 18
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(18)
<223> OTHER INFORMATION:

<400> SEQUENCE: 2
accagcgtgt ccaggaag                                            18

<210> SEQ ID NO 3
<211> LENGTH: 18
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(18)
<223> OTHER INFORMATION:

<400> SEQUENCE: 3
ccgccgcgag tgagggtt                                            18

```
<210> SEQ ID NO 4
<211> LENGTH: 23
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(23)
<223> OTHER INFORMATION:

<400> SEQUENCE: 4
tgcccatcat catgacctgg tct                                              23

<210> SEQ ID NO 5
<211> LENGTH: 22
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(22)
<223> OTHER INFORMATION:

<400> SEQUENCE: 5
cctaaaagcc accccacttc tc                                               22

<210> SEQ ID NO 6
<211> LENGTH: 22
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(22)
<223> OTHER INFORMATION:

<400> SEQUENCE: 6
atgctatcac ctcccctgtg tg                                               22

<210> SEQ ID NO 7
<211> LENGTH: 20
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(20)
<223> OTHER INFORMATION:

<400> SEQUENCE: 7
accacagtcc atgccatcac                                                  20

<210> SEQ ID NO 8
<211> LENGTH: 20
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(20)
<223> OTHER INFORMATION:

<400> SEQUENCE: 8
tccaccaccc tgttgctgta                                                  20
```

```
<210> SEQ ID NO 9
<211> LENGTH: 40
<212> TYPE: DNA
<213> ORGANISM: Artificial Sequence
<220> FEATURE:
<223> OTHER INFORMATION: Description of the artificial sequence: Probe
<220> FEATURE:
<221> NAME/KEY: misc_feature
<222> LOCATION: (1)..(40)
<223> OTHER INFORMATION:

<400> SEQUENCE: 9
gctccgccac tcgggcgctg cccatcatca tgacctggtc                              40

<210> SEQ ID NO 10
<211> LENGTH: 40
<212> TYPE: DNA
<213> ORGANISM: Artificial Sequence
<220> FEATURE:
<223> OTHER INFORMATION: Description of the artificial sequence: Probe
<220> FEATURE:
<221> NAME/KEY: misc_feature
<222> LOCATION: (1)..(40)
<223> OTHER INFORMATION:

<400> SEQUENCE: 10
gccactcggg cgctgcccat catcatgacc tggtcttcta                              40

<210> SEQ ID NO 11
<211> LENGTH: 40
<212> TYPE: DNA
<213> ORGANISM: Artificial Sequence
<220> FEATURE:
<223> OTHER INFORMATION: Description of the artificial sequence: Probe
<220> FEATURE:
<221> NAME/KEY: misc_feature
<222> LOCATION: (1)..(40)
<223> OTHER INFORMATION:

<400> SEQUENCE: 11
tcgggcgctg cccatcatca tgacctggtc ttctaggaag                              40

<210> SEQ ID NO 12
<211> LENGTH: 40
<212> TYPE: DNA
<213> ORGANISM: Artificial Sequence
<220> FEATURE:
<223> OTHER INFORMATION: Description of the artificial sequence: Probe
<220> FEATURE:
<221> NAME/KEY: misc_feature
<222> LOCATION: (1)..(40)
<223> OTHER INFORMATION:

<400> SEQUENCE: 12
cgctgcccat catcatgacc tggtcttcta ggaagcggct                              40

<210> SEQ ID NO 13
<211> LENGTH: 40
<212> TYPE: DNA
<213> ORGANISM: Artificial Sequence
<220> FEATURE:
<223> OTHER INFORMATION: Description of the artificial sequence: Probe
<220> FEATURE:
<221> NAME/KEY: misc_feature
<222> LOCATION: (1)..(40)
<223> OTHER INFORMATION:

<400> SEQUENCE: 13
cccatcatca tgacctggtc ttctaggaag cggctgctgc                              40
```

```
<210> SEQ ID NO 14
<211> LENGTH: 43
<212> TYPE: DNA
<213> ORGANISM: Artificial Sequence
<220> FEATURE:
<223> OTHER INFORMATION: Description of the artificial sequence: Probe
<220> FEATURE:
<221> NAME/KEY: misc_feature
<222> LOCATION: (1)..(43)
<223> OTHER INFORMATION:

<400> SEQUENCE: 14
catcatcatg acctggtctt ctaggaagcg gctgctgccc tag          43

<210> SEQ ID NO 15
<211> LENGTH: 32
<212> TYPE: DNA
<213> ORGANISM: Artificial Sequence
<220> FEATURE:
<223> OTHER INFORMATION: Description of the artificial sequence: Probe
<220> FEATURE:
<221> NAME/KEY: misc_feature
<222> LOCATION: (1)..(32)
<223> OTHER INFORMATION:

<400> SEQUENCE: 15
tgcccatcat catgacctgg tcttctagga ag                      32

<210> SEQ ID NO 16
<211> LENGTH: 42
<212> TYPE: DNA
<213> ORGANISM: Artificial Sequence
<220> FEATURE:
<223> OTHER INFORMATION: Description of the artificial sequence: Probe
<220> FEATURE:
<221> NAME/KEY: misc_feature
<222> LOCATION: (1)..(42)
<223> OTHER INFORMATION:

<400> SEQUENCE: 16
atcatcatga cctggtcttc taggaagcgg ctgctgccct ag           42

<210> SEQ ID NO 17
<211> LENGTH: 42
<212> TYPE: DNA
<213> ORGANISM: Artificial Sequence
<220> FEATURE:
<223> OTHER INFORMATION: Description of the artificial sequence: Probe
<220> FEATURE:
<221> NAME/KEY: misc_feature
<222> LOCATION: (1)..(42)
<223> OTHER INFORMATION:

<400> SEQUENCE: 17
ctccgccact cgggcgctgc ccatcatcat gacctggatc gg           42

<210> SEQ ID NO 18
<211> LENGTH: 39
<212> TYPE: DNA
<213> ORGANISM: Artificial Sequence
<220> FEATURE:
<223> OTHER INFORMATION: Description of the artificial sequence: Probe
<220> FEATURE:
<221> NAME/KEY: misc_feature
<222> LOCATION: (1)..(39)
<223> OTHER INFORMATION:

<400> SEQUENCE: 18
actcgggcgc tgcccatcat catgacctgg atcggcctc               39
```

```
<210> SEQ ID NO 19
<211> LENGTH: 39
<212> TYPE: DNA
<213> ORGANISM: Artificial Sequence
<220> FEATURE:
<223> OTHER INFORMATION: Description of the artificial sequence: Probe
<220> FEATURE:
<221> NAME/KEY: misc_feature
<222> LOCATION: (1)..(39)
<223> OTHER INFORMATION:

<400> SEQUENCE: 19
cgggcgctgc ccatcatcat gacctggatc ggcctccga                                39

<210> SEQ ID NO 20
<211> LENGTH: 40
<212> TYPE: DNA
<213> ORGANISM: Artificial Sequence
<220> FEATURE:
<223> OTHER INFORMATION: Description of the artificial sequence: Probe
<220> FEATURE:
<221> NAME/KEY: misc_feature
<222> LOCATION: (1)..(40)
<223> OTHER INFORMATION:

<400> SEQUENCE: 20
gctgcccatc atcatgacct ggatcggcct ccgaccgtaa                               40

<210> SEQ ID NO 21
<211> LENGTH: 40
<212> TYPE: DNA
<213> ORGANISM: Artificial Sequence
<220> FEATURE:
<223> OTHER INFORMATION: Description of the artificial sequence: Probe
<220> FEATURE:
<221> NAME/KEY: misc_feature
<222> LOCATION: (1)..(40)
<223> OTHER INFORMATION:

<400> SEQUENCE: 21
catcatcatg acctggatcg gcctccgacc gtaactattc                               40

<210> SEQ ID NO 22
<211> LENGTH: 44
<212> TYPE: DNA
<213> ORGANISM: Artificial Sequence
<220> FEATURE:
<223> OTHER INFORMATION: Description of the artificial sequence: Probe
<220> FEATURE:
<221> NAME/KEY: misc_feature
<222> LOCATION: (1)..(44)
<223> OTHER INFORMATION:

<400> SEQUENCE: 22
atcatcatga cctggatcgg cctccgaccg taactattcg gtgc                          44

<210> SEQ ID NO 23
<211> LENGTH: 45
<212> TYPE: DNA
<213> ORGANISM: Artificial Sequence
<220> FEATURE:
<223> OTHER INFORMATION: Description of the artificial sequence: Probe
<220> FEATURE:
<221> NAME/KEY: misc_feature
<222> LOCATION: (1)..(45)
<223> OTHER INFORMATION:

<400> SEQUENCE: 23
agcagctccg ccactcgggc gctgcccatc atcatgacct ggatc                         45
```

```
<210> SEQ ID NO 24
<211> LENGTH: 39
<212> TYPE: DNA
<213> ORGANISM: Artificial Sequence
<220> FEATURE:
<223> OTHER INFORMATION: Description of the artificial sequence: Probe
<220> FEATURE:
<221> NAME/KEY: misc_feature
<222> LOCATION: (1)..(39)
<223> OTHER INFORMATION:

<400> SEQUENCE: 24
atcatcatga cctggatcgg cctccgaccg taactattc                              39

<210> SEQ ID NO 25
<211> LENGTH: 41
<212> TYPE: DNA
<213> ORGANISM: Artificial Sequence
<220> FEATURE:
<223> OTHER INFORMATION: Description of the artificial sequence: Probe
<220> FEATURE:
<221> NAME/KEY: misc_feature
<222> LOCATION: (1)..(41)
<223> OTHER INFORMATION:

<400> SEQUENCE: 25
tcatcatgac ctggatcggc ctccgaccgt aactattcgg t                           41
```

METHOD FOR DETECTING NEOPLASTIC DISORDERS IN A SOLUBILIZED BODY SAMPLE

This application is a National Stage of International Application PCT/EP2004/051872, filed Aug. 20, 2004, published Sep. 22, 2005, under PCT Article 21(2) in English; which claims the priority of EP 03103218.8, filed Aug. 25, 2003.

The present invention relates to a method for the early diagnosis of neoplastic disorders such as cancers as well as their precursor stages, particularly cancers of the respiratory tract, the urinary system, the reproductive tract, cancer associated with HPV infection or cancer of the anogenital tract, from solubilized body samples.

BACKGROUND OF THE INVENTION

Preventive programs have been offered for the most differing cancers since the middle of the fifties. For cervical cancer an established population wide screening program exists in various developed countries. However similar screening programs are applicable for other cancer entities and the respective precursor stages such as e.g. cancers of the urinary system, of the respiratory tract and other. In the following cervical cancer is used as an example to highlight the drawbacks of the present preventive scenario. However the facts are mutandis mutatis applicable to other preventive programs for any cancer entity.

Regarding cervical intraepithelial neoplasia and cervical glandular lesions, the preventive programs are based mainly on the morphological and cytological examination of cytosmears of the cervix uteri, what is called the Pap test, which is made on the basis of gynecological routine examinations at regular intervals in women from the $20^{th}$ year on. By means of the morphology of the cells, the smears are divided into various intensity degrees of dysplastic cellular changes. According to Pap I-V, these intensity degrees are referred to as normal, mild dysplasia, fairly serious dysplasia, serious dysplasia and invasive carcinoma, respectively. If the Pap test leads to a striking result, a small biopsy will be taken and subjected to a histopathologic examination, by which the kind and intensity of the dysplasia are determined and classified as cervical intraepithelial neoplasia (CIN1-3).

In spite of all preventive programs, cervical cancer that lead to 400,000 new cases per year is the second most frequent neoplastic disorder in women. This is inter alia due to the fact that up to 30% of the results of individual Pap test are false-negative.

In conventional screening for cervical intraepithelial neoplasia, swabs are used for detection of neoplastic lesions of the cervix uteri. In the screening procedure, different kinds of lesions have to be distinguished. Causes for lesions may for example be inflammations (due to infectious agents or physical or chemical damage) or neoplastic disorders. In morphological examinations the lesions of different characteristics are sophisticated to distinguish. Thus, for examination of cervical swabs and smears cytologists and pathologists have to be especially trained, and even experienced examiners have a high inter- and intra-observer variance in the assessment of a diagnosis based on cytological specimens. In general, the result of the examination is based upon the subjective interpretation of diagnostic criteria by the examining pathologist/cytologist. As a result, the rate of false positive and false negative results in the screening tests remains unsatisfying high.

However, the reproducibility of the examination results may be enhanced by the use of supporting molecular tools. Yet the problem with the preservation and preparation of the samples may not be overcome by just additionally using molecular markers. One further complication when performing cytological or histological examinations for screening purposes and especially when applying methods for the detection of molecular markers originates from strict precautions in preserving the samples from causing artefacts or improper results.

This is in part due to the instability of the cell-based morphological information and in part to the instability of the molecular markers to be detected during the tests. If the samples are not prepared, transported or stored in an appropriate manner, the cell-based information, or even the molecular information may be lost, or may be altered. So the diagnosis may be impossible, or may be prone to artefacts. For example, the interpretation of biopsies or cytological preparations is frequently made difficult or impossible by damaged (physically or bio/chemically) cells. Furthermore regarding tissue samples or biopsies, the preservation of molecular constituents of the samples, which are subject to a rapid turnover, is sophisticated due to the time passing by until penetration of the total sample by appropriate preservatives.

Although the above is shown using cervical cancer as an example the overall background also applies to preventive programs of neoplastic disorders in general as the situation for other cancer entities is very much the same. Generally the morphologically supported diagnostic methods performed routinely in the art show two major disadvantages. Firstly, the methods are highly dependent on individual perception of the examiners. Secondly, the morphological information is quite sensitive to decay processes and thus to production of artefacts after preparation of the samples. Both aspects contribute to improper reproducibility of the results.

Therefore, it is the object of the present invention to provide a method by which neoplastic disorders such as cancers and their precursor stages can be diagnosed early and reliably. In addition, a differentiation should be possible by this method with respect to benign inflammatory or metaplastic changes from neoplastic disorders such as dysplastic lesions and precancers. Moreover, the present invention provides methods for the detection of cancers on a biochemical basis from solubilized samples. The samples may be of any kind including cells in a cell preservation solution as is used for Liquid based cytology methods.

The inventors insight that use of LBC samples as a source of sample material for the development of diagnostic test kits for the biochemical non-cell based assessment of diagnosis of medically relevant conditions is another aspect of the present invention. In the art LBC samples are used for development of cell based assay formats. Lysis of the samples in a way as disclosed herein however enables inventors to base the development of the biochemical kits on sample material which is suited to provide information on the patients disease status from other diagnostic procedures on the same sample material.

A method for detection of HPV nucleic acids from LBC samples is disclosed by Digene Corp. This method uses LBC samples as basis for the analysis. Detection of the HPV nucleic acids is performed after lysis of the cells contained in the LBC samples. In this method no normalization of the amount of the LBC sample to be employed in the biochemical non-cell based detection of the HPV nucleic acid, is performed with respect to information obtained from the cytological specimen prepared out of the same LBC sample. The method disclosed by Digene is therefore restricted to mere qualitative measurements. Any biochemical non-cell based quantitative or even semiquantitative method needs information on the composition of the samples obtainable either from biochemical markers or from the microscopic or flow cytometric analysis of the sample. In the present invention the use of LBC samples for the assessment of diagnosis or for development of kits and in-vitro diagnostic devices enables for an accurate and comparable way to provide cytological information for the biochemical non-cell based testing. The employment of biochemical normalization with respect to markers indicative for the presence or absence of cells or cell types is omissible. The advantage of using LBC samples in this respect is that the cytologically cell based information is directly related to the homogeneous LBC specimen and thus provides valuable accurate information for use in the evaluation of the biochemical non-cell based test results.

A method for detection of molecular markers on the protein or nucleic acid level from solubilized specimens on the other hand is disclosed in various publications. However no link to the use of LBC samples as a source of the sample specimen in made in this respect. Generally LBC methods are applied in the art to enable for improved morphological evaluation of cytology specimens. The field of application of the LBC samples is therefore indicated only for cytology. Based on the disclosure in the prior art preparation of an LBC sample for subsequent solubilization of the sample for biochemical testing is not disclosed. Moreover the disclosure as to the advantages of LBC procedures teach away from application of LBC samples in any method that is not founded on cellular morphological evaluation of the specimens. According to the inventors findings the use of LBC samples as a source for biochemical non-cell based determination of protein levels in solubilized specimens provides the advantage that the results may be directly compared to a cytological specimen. The protein based biochemical analysis in this respect may serve as a e.g. pre-testing or to provide further information or even to confirm a cytologically equivocal result. In further embodiments the information obtained from the biochemical non-cell based testing may be for the design of the cytological procedures to be applied.

The development method disclosed herein is therefore of great value for achieving effective and reliable kits and in-vitro diagnostic devices. The method for development of kits and in-vitro diagnostic devices as disclosed herein achieves comparability of the results generated by biochemical non-cell based analysis with the cytologically assessed results by means of a normalization. This normalization of the sample for application in the biochemical test format is performed with respect to information on the LBC sample obtainable from the cytological specimen prepared from the LBC sample. Such information comprises e.g. cellularity of the LBC sample, information with respect to volume of the LBC sample, information with respect to mass of the LBC sample or with respect to parameters accessible only via the generation of a thin-layer specimen out of the LBC sample. In this respect the inventors provide by the methods as claimed herein a reliable method for development of kits and in-vitro diagnostic devices on the basis of LBC samples.

SUMMARY OF THE INVENTION

The present invention is directed to a method for detecting neoplastic disorders from a solubilized body sample of a human subject. The method comprises the steps of: (a) obtaining a body sample from a human subject, (b) solubilizing the body sample in a lysis medium, and (c) determining the overexpression of a cyclin-dependent kinase inhibitor in the solubilized body sample by comparing the level of said cyclin-dependent kinase inhibitor within said solubilized body sample with the level present in a solubilized healthy human body sample. The samples for use in the method of the present invention may be of any kind including cells in a cell preservation solution as is used for Liquid based cytology methods.

The present invention is further directed to a test kit for determining the level of cyclin-dependent kinase inhibitors comprising probes specific for said cyclin-dependent kinase inhibitor and a lysis medium for solubiliation of a body sample. The test kit may be an in-vitro diagnostic device.

In certain embodiments of the present invention the kit is provided as an in-vitro diagnostic device. Therefore the present invention is also directed to an in-vitro diagnostic device comprising probes directed against a cyclin-dependent kinase inhibitor fixed on solid carriers, for measuring the cyclin-dependent kinase inhibitor in a solubilized sample.

The present invention is furthermore directed to a method of development of kits and in-vitro diagnostic devices for assessment of diagnosis of medically relevant conditions from solubilized body samples, wherein the development is performed using body samples provided as preserved cells in a cell-preservation medium and wherein the preserved cells are intended and prepared for use in cytological examination processes such as Liquid Based Cytology processes. The samples intended for Liquid Based Cytology processes (in the following denominated as LBC samples) are solubilized in an appropriate lysis medium and are used for development activities of kits and in-vitro diagnostic devices for detection of medically relevant conditions from solubilized body samples on the basis of biochemical non-cell-based analysis.

The present invention is also directed to a method for assessment of diagnosis of medically relevant conditions by biochemical non-cell-based analysis of the presence or absence and or the level of marker molecule in solubilized body samples, wherein the body sample is an LBC sample, and wherein the detection of marker molecules is carried out by detection of the presence or absence and or the level of proteins, peptides, nucleic acids or fragments thereof in said solubilized samples. The marker molecules that may be applied for this method are disclosed above as "marker molecules characteristic for medically relevant conditions". The method may be applied to any medically relevant condition.

DETAILED DESCRIPTION OF THE INVENTION

Figure 1:
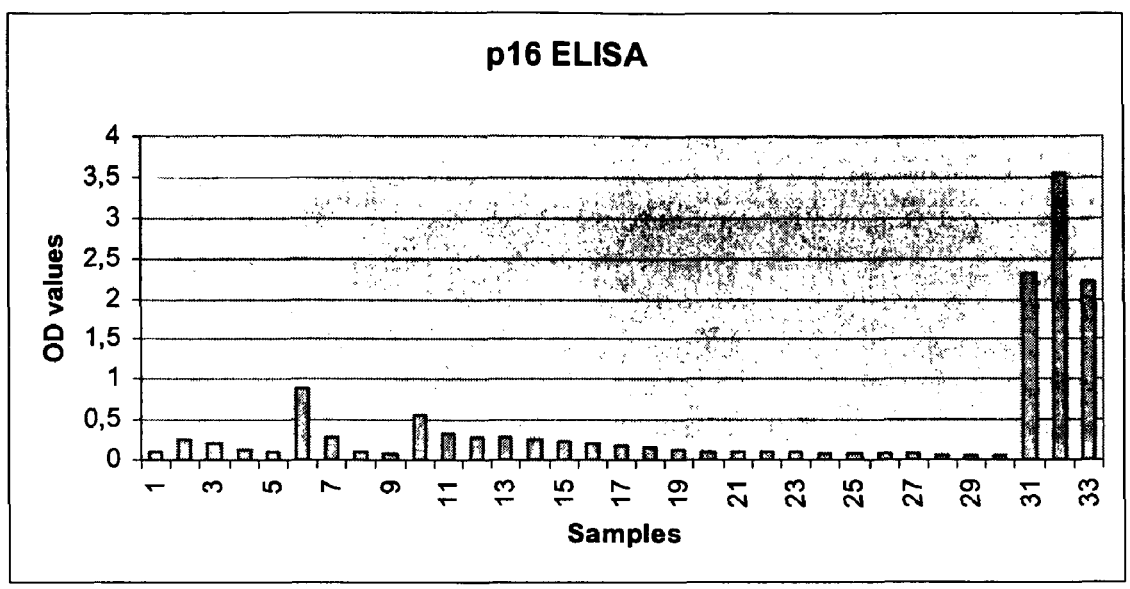
FIG. 1 shows the OD values returned in an ELISA test detecting the level of p16$^{INK4a}$ in solubilized cervical samples; for experimental details see Example 1.

The present invention is based on the applicant's insights that cyclin-dependent kinase inhibitor gene products are overexpressed in many neoplastic disorders such as cancers, e.g. cancers of the respiratory tract, cancers of the reproductive tract, cancers of the urinary system, HPV associated cancers or anogenital cancers, particularly cervical cancer, and precursor stages of these cancers, respectively. Examples of the cyclin-dependent kinase inhibitors are the proteins p14, p15$^{INK4b}$, p16$^{INK4a}$, p18$^{INK4c}$, p19$^{INK4d}$, p21$^{WAF1/CIP1}$ and p27$^{KIP1}$. The cell cycle regulatory protein p14$^{ARF}$, which is by function not a cyclin-dependent kinase inhibitor, shall within the context of the present invention be included in the expression "cyclin-dependent kinase inhibitor".

The applicant has found that the intensity of cyclin-dependent kinase inhibitor overexpression as detected in cytological specimens correlates with the degree of dysplasia as detected in corresponding histological specimens.

According to the invention, the applicant's insights are used for a method for the early diagnosis of neoplastic disorders such as cancers and their precursor stages, which comprises determining the overexpression of cyclin-dependent kinase inhibitors in a body sample.

According to the invention, cytological and/or histological examination procedures may be supported or even substituted by the use of molecular markers. Such markers may e.g. be used in immuno-cytochemical staining reactions, or in the course of in-situ hybridization reactions. Combinations of morphological examinations and immuno-cytochemical staining reactions based on marker molecules, characteristic for neoplastic disorders such as cancers, e.g. of the cervix uteri, the bladder or the lung, may lead to enhanced results. The morphologic examination remains laborious and time consuming and thus expensive, even when supported by the molecular methods, that make the results more reliable. Additionally, the diagnosis on a morphologically cell based level is, even when supported by molecular parameters, subject to individual perception of the morphology by individual examiners. Thus the diagnosis is dependent on the person, that performs the examinations.

The inventors moreover could show that in specific cases molecular markers may be used as diagnostic tools without further support by cell based morphological examinations. Methods for diagnosis of neoplastic disorders such as cancers on a molecular level only, without the support of cell based information, are restricted to cases, where markers or levels of markers are specific for the condition to be characterized. This is especially true, if the markers are non-human substances. For example detection of viral infections may be carried out in solutions of samples, because the markers characteristic for the presence of viruses in tissues do not occur in unaffected human tissues.

However, the inventors found that certain human cyclin-dependent kinase inhibitors may serve as a marker for cancers in biochemical marker based detection procedures although it is a cell cycle regulatory protein being expressed at low levels in any normally proliferating human cell in certain stages of the cell cycle.

Cyclin-dependent inhibitors for use in the present invention comprise the cyclin-dependent kinase inhibitors p14, $p15^{INK4b}$, $p16^{INK4a}$, $p18^{INK4c}$, $p19^{INK4d}$, $p21^{WAF1/CIP1}$ and $p27^{KIP1}$. Beside cyclin-dependent kinase inhibitors the cell cycle regulatory protein $p14^{ARF}$ encoded by an alternative reading frame of the $p16^{INK4a}$ gene may also be used for a method as disclosed herein. For convenience, within the context of the present invention the cell cycle regulatory protein $p14^{ARF}$, which is by function not a cyclin-dependent kinase inhibitor, shall be included in the expression "cyclin-dependent kinase inhibitor".

"p16" or "cyclin-dependent kinase inhibitor $p16^{INK4a}$" as used herein refers to cyclin-dependent kinase inhibitor $p16^{INK4a}$ (also denominated as CDKN2 or MTS1) the gene of which is located in chromosomal region 9p21. $p16^{INK4a}$ was first described in Serrano, M., et al., Nature, 1993 Dec. 16; 366(6456): 704-7. The terms "$p16^{INK4a}$" or "cyclin-dependent kinase inhibitor $p16^{INK4a}$" in all their grammatical forms as used in the context of the present invention refers to nucleic acid as well as polypeptide molecules. "$p16^{INK4a}$" or "cyclin-dependent kinase inhibitor $p16^{INK4a}$" thus comprises e.g. RNA (mRNA, hnRNA, etc.), DNA (cDNA, genomic DNA, etc.), proteins, polypeptides, proteoglycans, glycoproteins and the respective fragments of these molecules.

The "level" of cyclin-dependent kinase inhibitors or other marker molecules as uses herein refers to a semiquantitative as well as a quantitative value regarding the amount of the marker (cyclin-dependent kinase inhibitors or other marker molecules) present in a sample. A quantitative value may e.g. be represented in terms of a concentration. A semi-quantitative value may be expressed in terms of a scale of levels e.g. undetectable levels, low levels, intermediate levels, high levels or any other suitable mode. The level of a marker such as e.g. $p16^{INK4a}$ may also be represented in terms of a dependent parameter such as the intensity of a signal generated in an assay format in response to the presence of e.g. a cyclin-dependent kinase inhibitor. In certain embodiments the level may also refer to a qualitative determination of the presence of a marker molecule.

Due to the expression of cyclin-dependent kinase inhibitors (e.g. $p16^{INK4a}$) in certain benign cell types present in body samples (e.g. cervical specimens, specimens from the oral cavity, urine, sputum etc.), the diagnosis of neoplastic disorders based on the level of cyclin-dependent kinase inhibitors without additional information on the cellular morphology seem to be difficult or impossible. It was known in the art that in up to 30% of cervical specimens, few to many metaplastic cells may be immunoreactive for cyclin-dependent kinase inhibitor $p16^{INK4a}$ at a moderate to high level. Moreover, endometrial cells that may under certain circumstances be present in cervical swabs may be positive for $p16^{INK4a}$. In cytological or histological testing procedures, this fact does not influence the diagnosis, because the cell types may easily be distinguished from dysplastic cells with respect to their cellular morphology.

Surprisingly the inventors found that by defining a threshold value of cyclin-dependent kinase inhibitors (e.g. $p16^{INK4a}$), it is possible to enable the detection or diagnosis of dysplasias even without knowledge of the cellular morphology.

The expression "neoplastic disorders" in all its grammatical forms as used in the context of the present invention refers to cancers of any kind and origin and precursor stages thereof, respectively. Accordingly the term "neoplastic disorder" shall comprise the subject matter identified by the terms "neoplasia", "neoplasm", "cancer", "precancer" or "tumor". Also the cytological counterpart to histological conditions identified as "dysplastic" or as "dysplasia" shall be within the scope of the term "neoplastic disorder" as used herein.

Neoplastic disorders to which the methods of the present invention may be applied comprise for example, neoplastic lesions of the respiratory tract, of the urinary system, of the gastrointestinal tract of the anogenital tract, neoplastic disorders associated with HPV infection and others. They may be cancers of the respiratory tract, the urinary system, the reproductive tract or anogenital cancers, HPV associated cancers and particularly the cervical cancer. In connection with the latter, its precursor stages, e.g. cervical intraepithelial neoplasias (CINI-III), carcinomas in situ (CIS), etc., have to be mentioned particularly. The term "precursor stages" in all it's grammatical forms as used herein comprises all precursor stages and precursors of cancers or any other malignancies. With respect to cervical cancer precursor or preliminary stages as used herein may e.g. refer to stages of cervical intraepithelial neoplasias as identified by appropriate classification systems such as e.g. the CIN classification (CIN I-CIN III) the PAP classification (PAP I-PAP V) or the Bethesda Classification (NILM, LSIL, HSIL).

With respect to cancers of the respiratory tract cancers may comprise any malignant condition of the respiratory tract such as, e.g., cancer of the lung, the alveoles, the bronchioles, the bronchial tree and the broncus, the nasopharyngeal space, the oral cavity, the pharynx, the nasal cavity and the paranasal sinus. Lung cancer such as small cell lung cancer, non-small cell lung cancer, squamous cell lung carcinoma, small cell lung carcinoma, adenocarcinoma of the lung, large cell lung carcinoma, adeno-squamous lung carcinoma, carcinoid tumor of the lung, broncheal gland tumor or (malignant) mesothelioma. An overview over tumors of the respiratory tract may be found in Colby T V, et al.: Tumors of the Lower RespiratoryTract, Atlas of Tumor Pathology, Third Series, Fascicle 13, AFIP: Washington 1995," which shall be incorporated herein by reference.

Tumors of the urinary system may comprise bladder cancer, cancer of the kidney, renal pelvis, cancer of the ureters and cancer of the urethra, etc. Tumors of the reproductive system may comprise cancer and precursory stages thereof of the ovary, the uterus, the testis, the prostate, the epididymis, etc.

In certain embodiments of the invention neoplastic disorder shall refer generally to HPV associated neoplastic disorders. The invention in this respect is applicable to neoplastic disorders associated with HPV and especially high risk HPV types and mucosal HPV types. The high risk HPV may comprise HPV subtypes such as e.g. HPV 16, 18, 31, 33, 35, 39, 45, 51, 52, 56 and 58. Markers for HPV infection may e.g. comprise HPV expression products of HPV genes L1, L2, E2, E4, E5, E6 or E7.

The expression "body sample" comprises any body samples of any kind and nature. Examples of such body samples are secretions, swabs, lavages, body fluids, semen, cell- and tissue-samples, blood, smears, sputum, urine, stool, liquor cerebrospinalis, bile, gastrointestinal secretions, lymph, bone marrow, aspirates and biopsies of organs such as needle or punch biopsies and (fine)-needle aspirates. In particular, smears, swabs and biopsies are indicated when the detection of anogenital cancers, e.g. cervical cancers, is concerned. The term biopsies as used throughout this text shall comprise all kind of biopsies known to those of skill in the art. Thus biopsies as used in the context of the present invention may comprise e.g. resection samples of tumors, tissue samples prepared by endoscopic means or punch- or needle-biopsies of organs. Biopsies comprises specimens obtained by several different methods such as cold knife biopsies, LEEP (loop electrocautery excisional procedure) biopsies, etc.

Body samples as used in the context of the present invention may comprise fixed or preserved cell or tissue samples. Cell or tissue samples may e.g. be preserved in a standard sample collection, storage or transportation medium, known to those of skill in the art such as e.g. commercially available preservation media (formalin solution, Cytyc "PreservCyt" or "CytoLyt", Digene "Universal Collection Medium", Tripath Imaging "Cytoricho", etc.). In one embodiment of the invention the cell or tissue samples provided in standard sample collection media are liquid based cytology samples (LBC samples) which are prepared according to or analogous to the methods employed for cytological LBC methods known to those of skill in the art. Suitable cell preservation media may contain a mixture of one or more selected from a group comprising alcohols, aldehydes, ketones, acids, metal-ions or sublimates, ethers etc. for preservation of cellular components. Alcohols include methanol, ethanol, (n- or i-) propanol, (n-, i- or t-) butanol or higher branched or unbranched alcohols. Aldehydes include formaldehyde, acetaldehyde, glutaraldehyde, etc. Ketones such as Acetone may be used. Acids for use in standard sample media include organic acids (acetic acid, trichloro-acetic acid, salicylic acid, picric acid) or inorganic acids such as e.g. chromic acid. Standard sample solutions may comprise metals such as silver, copper, chromium, mercury, osmium, uranium. Solutions of salts such as uranyl-acetate, potassiumbichromate, ammonium sulfate, etc. may be components of preservative media.

Cells preserved in suitable media (alcohols etc.) or fixed tissue samples may be used as raw samples in the methods according to the present invention. In one embodiment, the body sample may e.g. comprise a sputum sample, a cervical swab, an oral swab, an urethral swab or the like that has been transferred to a preservative medium containing alcohol.

Furthermore, body samples that have been subjected to cell lysing conditions immediately after obtaining the samples may be used in the methods disclosed herein. Inventors have found a number of robust, fast and easy ways to preserve molecular properties of samples, in which the morphological information of samples is lost. Samples may be e.g. prepared in a reproducible and easy to store and to transport form by solubilizing the cellular components of the raw sample in a suitable lysis medium immediately after or even during obtaining the sample. Body fluids may directly be transferred from the body of an individual to a medium containing suitable detergents and preservative substances. Furthermore, tissue samples may immediately be transferred to denaturing lysis conditions (eventually supported by physical forces) and be thus preserved. Using appropriate ingredients in the lysis medium, the molecular components of the original sample may be preserved, and no degradation may occur. The degradation by enzymatic activities may for example be minimized by the use of enzyme inhibitors. Thus, a solution of test samples in said lysis medium may represent the molecular properties of a test sample at the time of solubilization.

According to the present invention, the body samples may be solubilized in any suitable lysis medium. Such lysis media may far example be aqueous solutions of chaotropic agents such as e.g. urea, GuaSCN, Formamid, of detergents such as anionic detergents (e.g. SDS, N-lauryl sarcosine, sodium deoxycholate, alkyl-aryl sulphonates, long chain (fatty) alcohol sulphates, olefine sulphates and sulphonates, alpha olefine sulphates and sulphonates, sulphated monoglycerides, sulphated ethers, sulphosuccinates, alkane sulphonates, phosphate esters, alkyl isothionates, sucrose esters), cationic detergents (e.g. cetyl trimethylammonium chloride), non-ionic detergents (e.g. Tween 20, Nonidet P40, Triton X-100, NP40, Igepal CA-630, N-Octyl-Glucosid) or amphoteric detergents (e.g CHAPS, 3-Dodecyl-dimethylammonio-propane-1-sultanate, Lauryidimethylamine oxide) and/or of alkali hydroxides such as e.g. NaOH or KOH. Generally any suitable liquid may be used as a solvent in the lysis medium of the present invention. The liquid may be organic or inorganic and may be a pure liquid, a mixture of liquids or a solution of substances in the liquid and may contain additional substances to enhance the properties of the solvent. In certain embodiments, where lysis of cells may be achieved without the use of detergents, hyper- or hypotonic solutions or buffers or simply water or an organic liquid may be used as solvent. Any liquid, that is suited to solubilize the cellular components of body samples in total or in parts may be regarded as a lysis medium as used herein. Thus lysis media as used herein need not contain buffer substances or have buffer capacity. However in certain embodiments of the invention the lysis media may have buffer capacity and may contain buffer substances.

In one embodiment, the lysis medium is designed, so that cells, cell debris, nucleic acids, polypeptides, lipids and other biomolecules potentially present in the raw sample are solubilized. In further embodiments of the present invention, the solvent may be designed to assure differential solubilization of specific components of the body sample, leaving other components unsolubilized.

The lysis medium for solubilizing the body sample according to the present invention may furthermore comprise one or more agents that prevent the degradation of components within the raw samples. Such components may for example comprise enzyme inhibitors such as proteinase inhibitors, RNAse inhibitors, DNAse inhibitors, etc. In one embodiment of the present invention, the sample is lysed directly in the form obtained from test-individuals. Proteinase inhibitors may e.g. comprise inhibitors of serine proteinases, inhibitors of cysteine proteinases, inhibitors of aspartic proteinases, inhibitors of metally proteinases, inhibitors of acidic proteinases, inhibitors of alkaline proteinases or inhibitors of neutral proteinases. In certain embodiments of the present invention the inhibition of enzymes may be achieved by chemical means such as e.g. denaturation of the enzymes by means of salt concentration, pH, chaotropic agents or the like.

In another embodiment of the present invention the body sample may be further purified before being lysed. Such purification procedures may for example comprise washing away of contaminants such as mucus or the like, separation or concentration of cellular components, preserving and transporting of the cells. In one embodiment for example the cells may be separated by means of flow cytometry or other suitable forms of cell sorting known to those of skill in the art. Thus the cellular components of the raw samples are included in a single sample solution.

The preparation of a sample for use in a method as disclosed herein may also comprise several steps of further preparations of the sample, such as separation of insoluble components, isolation of polypeptides or nucleic acids, preparation of solid phase fixed peptides or nucleic acids or preparation of beads, membranes or slides to which the molecules to be determined are coupled covalently or non-covalently.

The expression "determining the overexpression of cyclin-dependent kinase inhibitors proteins" comprises any methods which are suited for detecting the expression of cyclin-dependent kinase inhibitor proteins or their encoding mRNAs and an amplification of the corresponding genes, respectively. In order to determine an overexpression, the body sample to be examined may be compared with a corresponding body sample which originates from a healthy person or from a non-diseased region of the respective organ. Such a sample can be present in a standardized form.

The comparison with normal healthy body samples may be achieved by different methods. In one embodiment of the present invention, the comparison may be performed directly by including a control reaction with non-diseased tissue or cell sample. This non-diseased tissue or cell samples may be provided from a healthy person or from non-diseased regions of the human subject under examination or from cell culture cells known to show the properties of non-diseased cells with respect to cyclin-dependent kinase inhibitor expression. In another embodiment, the comparison may be performed indirectly by comparing the level of cyclin-dependent kinase inhibitor within the sample under investigation to a level of said cyclin-dependent kinase inhibitor known to be present in normal healthy samples. The knowledge about the level for normal healthy issue or cell samples may be derived from a representative number of testings or from scientific publications providing information the expression level of said cyclin-dependent kinase inhibitor in normal healthy cells. Comparison may be performed by employing a value for the concentration of the cyclin-dependent kinase inhibitors protein or nucleic acids; otherwise a characteristic value depending on the protein or nucleic acid concentration such as the optical density under defined reaction conditions may be employed. Otherwise the known value may be represented by a surrogate control such as a peptide or a recombinant protein. Thus the level of $p16^{INK4a}$ present in normal healthy samples may be represented by a control sample of a recombinant protein or a peptide in the testing procedure.

Generally, the comparison of the level present in the sample under investigation may be performed with respect to a value determined in each single testing procedure or to a predetermined value. The predetermined value may be determined for the testing procedure globally. Otherwise, the value may be valid only for a certain lot of testing reagents. For example, the reference value may be valid for a defined calibration period only and may be defined upon calibration of the testing process.

For example the level of cyclin-dependent kinase inhibitor in a healthy human cervical sample can be determined from a standardized sample solution. A standardized sample solution may comprise a solution of a solubilized pool of normal cell or normal tissue samples. The sample pool may, e.g., be a pool of cytological specimens with pre-assessed normal diagnosis from a screening population, or a pool of normal cells obtained from histological specimens. Furthermore, a pool of normal cells may be obtained from tissue culture of normal cervical epithelial cells. The sample solution may, e.g., be standardized with respect to the content of cells per ml sample solution. Any other parameter for standardization may be applied. The sample solution may e.g. be provided in a standardized form to ensure stability and reproducibility of the test results. In certain embodiments such solution may be provided as a component of the kit for comparison or calibration purposes.

In certain embodiments, the step of comparing the level of cyclin-dependent kinase inhibitors present in a patient sample to a level known to be present in a normal healthy body sample is embodied as employing a cut-off value or threshold value for the concentration of the respective cyclin-dependent kinase inhibitor. The cut-off in this context is a value (for example a concentration of $p16^{INK4a}$ protein given in e.g. mg/ml or an optical density measured under defined conditions in an ELISA test) which is suited to separate normal healthy samples from diseased samples. e.g. all samples giving values above the cut-off value are considered to be dysplastic, whereas the samples giving values below the cut-off value are considered to be healthy.

In certain embodiments, the threshold or cut-off may be set in a way to separate high grade neoplastic disorders (HSIL or neoplastic disorders corresponding e.g. to invasive carcinoma, high grade dysplasia or histologically assessed CIN 3 lesions) from all less severe stages of neoplastic disorders (e.g. LSIL). In other embodiments, the cut-off may be defined to differentiate healthy samples (NILM) from neoplastic disorders including precursory stages (LSIL and HSIL). It is thus possible to tailor the testing format in order to fit different tasks such as early detection of lesions and even precursors of the lesions or detection of lesions that deserve immediate therapy.

The (over) expression of cyclin-dependent kinase inhibitors can be detected on a nucleic acid level and protein level, respectively. Regarding the detection on a protein level: it is possible to use e.g. antibodies which are directed against cyclin-dependent kinase inhibitors. These antibodies can be used in the most varying methods such as Western blot, ELISA or immunoprecipitation. It may be favorable for the antibodies to be fixed on solid carriers such as ELISA plates, reaction vessels, beads, spheres, membranes, colloids such as colloidal metals (e.g. gold), porous members, surfaces of capillaries (e.g. in flow through test), test strips or latex particles. Regarding detection on the nudeic acid level methods such as nucleic acid amplification techniques or hybridization techniques may be applied. Nucleic acid amplification techniques comprise all kinds of single step or multistep reactions such as chain reactions. Chain reactions comprise but are not limited to PCR, NASBA, RT PCR, LCR etc. Hybridization reactions comprise any hybridization reactions with any kind of reporter system. Hybrid capture reactions with subsequent detection of hybrid nucleic acids by means of antibodies, directed against said hybrids. Examples for application of hybridization reactions for detection of expression on the level of RNA transcripts such as e.g. RNA in-situ hybridization reactions.

In certain embodiments of the present invention, the detection of the marker molecules is performed from a solution of solubilized body samples. Therefore detection may be carried out in solution or using reagents fixed to a solid phase.

A solid phase as used in the context of the present invention may comprise various embodiments of solid substances such as planar surfaces, particles including micro-, nano-particles or even smaller particles). In certain embodiments, particles may be provided as spheres, beads, colloids, or the like.

The fixation of reagents to the solid phase in a test kit or an in-vitro diagnostic device may be carried out via direct fixation or via indirect fixation. Direct fixation may be carried out by covalent binding, non-covalent binding, association, or adsorption to surfaces. Indirect fixation may be carried out through binding of the antibody to agents which themselves are directly fixed to solid phases. Binding agents, for example, include avidin, streptavidin, biotin, digioxingenin, antibodies or the like.

The detection of one or more molecular markers may be performed in a single reaction mixture or in two or more separate reaction mixtures. The detection reactions for several marker molecules may for example be performed simultaneously in multi-well reaction vessels. The detection reaction for marker molecules may comprise one or more further reactions with detecting agents either recognizing the initial marker molecules or preferably recognizing the prior molecules (e.g. primary antibodies) used to recognize the initial markers. The detection reaction further may comprise a reporter reaction indicating the level of the markers characteristic for cell proliferative disorders or the normalization markers.

The detection reaction for detecting the level of cyclin-dependent kinase inhibitor in solubilized samples may be carried out in solution or with reagents fixed to solid phases. In certain embodiments, the detection reaction may be carried out in solution; such procedures may comprise any methods suited for the detection of molecular interactions (binding of an antibody or similar binding agent to an antigen) in solution. The methods for determination of molecular interaction (change in conductivity, mass changes, light-, UV-, IR-, magnetic spectrometric changes, plasmon resonance, etc.) are known to those of skill in the art. In certain embodiments the detection may comprise a method where a complex of detection reagent bound to antigen is adsorbed to a solid phase for detection purpose. Thus, non-covalent bonding of the analytes to solid phases in the course of the detection reaction or even before starting the detection reaction may be used in a method according to the present invention.

A probe for the detection of the marker molecules may be any molecule, that specifically binds to said marker molecules. The probe may for example be an antigen binding agent such as antibodies (monoclonal or polyclonal), antibody fragments or artificial molecules comprising antigen binding epitopes, DNA or RNA binding molecules such as proteins or nucleic acids. Nucleic acids binding to other nucleic acids may for example be oligonucleotides for detection purposes or primers. In certain embodiments even larger nucleotide molecules may be applied for hybridization reactions. A molecule is said to recognize another molecule if it specifically interacts with that molecule. Specific interaction may for example be specific binding to or of the other molecule. The term "antibody" in all its grammatical forms shall in the context of the present invention refer generally to antigen binding molecules including but not limited to monoclonal and polyclonal antibodies, fragments of antibodies, antigen binding epitopes, mini-antibodies, peptidomimetics with antigen-binding properties, anticalines and diabodies.

The reporter reaction may be any event producing a signal in response to the presence of the marker or to the binding of a specific probe to the marker. For example, a reaction producing a colored compound, a fluorescent compound, a light emitting compound, a radiation emitting compound, or the concentration of one or more of these compounds to a detectable concentration in a predefined area of a testing device may serve as reporter reaction.

Applicable formats for the detection reaction according to the present invention may be blotting techniques, such as Western-Blot, Southern-blot, Northern-blot. The bloffing techniques are known to those of ordinary skill in the art and may be performed for example as electro-blots, semidry-blots, vacuum-blots or dot-blots. Furthermore immunological methods for detection of molecules may be applied, such as for example immunoprecipitation or immunological assays, such as EIA, ELISA, RIA, FIA (fluorescent immunoassay) lateral flow assays (using porous members or capillaries), immunochromatographic strips, flow through assays, latex agglutination assays etc. Immunoassays for use in the invention may comprise competitive as well as non-competitive immunoassays, such as sandwich assays.

In nucleic acid based approaches hybridization or amplification techniques may be applied. Hybridization techniques may e.g. comprise any hybridization technique known to those of skill in the art. In certain embodiment the hybridization may be carried out as a hybrid capture assay employing antibodies directed against DNA-RNA hybrid molecules for detection. Amplification reaction may be applied as PCR, NASBA, RT-PCR, LCR or other suitable chain reactions. Otherwise even single step or sequential reactions not being chain reaction may be applied for nucleic acid amplification.

In certain embodiments of the invention, immunochemical or nucleic acid based testing may be performed using a testing device for clinical laboratories. Such testing device may comprise any device suitable for immunochemical or nucleic acid based testing including any format such as point of care testing devices as well as bench top or laboratory devices. The devices may be e.g. provided as open or closed platform systems. The system may be based on any suitable methodology such as microtiter plates, multiwell plates, flow through or lateral flow systems, microchip or array based systems or bead or membrane based systems. The detection methods employed may comprise any methods known to those of skill in the art useful for immunochemical or nucleic acids based detection reactions. Such detection systems may be e.g. luminescence systems (electroluminescence, bioluminescence, photoluminescence, radioluminescence, chemiluminescence, electrochemoluminescence), fluorescence based systems, conductivity based detection systems, radiation (light, UV, X-ray, gamma etc.), plasmon resonance (e.g. Surface Plasmon Resonance SPR) or any other known method.

The term porous member as used herein shall generally apply to any three dimensional arrangements of porous substances. Such porous member may e.g. comprise compounds as membranes, beads or other.

By means of the present invention it is possible to diagnose cancers early, i.e. in their precursor stages.

A further subject matter of the present invention relates to a kit for carrying out a method according to the invention. Such a kit comprises e.g.:

(a) a reagent for detecting the expression of a cyclin-dependent kinase inhibitor, e.g. a probe directed against a cyclin-dependent kinase inhibitor protein or nucleic acid and parts thereof, respectively, (b) a lysis medium for solubilization of a body sample, (c) conventional auxiliary agents, such as buffers, carriers, markers, etc., and optionally (d) an agent for control reactions, e.g. a cyclin-dependent kinase inhibitor protein or nucleic acid and parts thereof, respectively, or a preparation of cells.

Furthermore, one or several of the individual components may be present For example, the detection reagent and other reagents fixed to a solid phase may be present. In one embodiment of the present invention the kit comprises a reagent for detection of $p16^{INK4a}$ fixed to solid phases and no detection reagents of other specificities fixed to solid phases.

In certain embodiments of the invention the kits for detection of cyclin-dependent kinase inhibitors are provided as in-vitro diagnostic devices.

Generally, the lysis medium included in a kit according to the present invention may be any suitable solvent known to those of skill in the art. The lysis medium for use in the kit may, for example, be organic or aqueous solutions of chaotropic agents such as e.g. urea, GuaSCN, Formamid, of detergents such as anionic detergents (e.g. SDS, N-lauryl sarcosine, sodium deoxycholate, alkyl-aryl sulphonates, long chain (fatty) alcohol sulphates, olefine sulphates and sulphonates, alpha olefine sulphates and sulphonates, sulphated monoglycerides, sulphated ethers, sulphosuccinates, alkane sulphonates, phosphate esters, alkyl isethionates, sucrose esters), cationic detergents (e.g. cetyl trimethylammonium chloride), non-ionic detergents (e.g. Tween 20, Nonidet P40, Triton X-100, NP40, Igepal CA-630, N-Octyl-Glucosid) or amphoteric detergents (e.g CHAPS, 3-Dodecyl-dimethylammonio-propane-1-sulfonate, Lauryldimethylamine oxide) and/or of alkali hydroxides such as e.g. NaOH or KOH. In certain embodiments, where lysis of cells may be achieved without the use of detergents, hyper- or hypotonic solutions or buffers or simply water or an organic liquid may be used as solvent. Any liquid, that is suited to solubilize the cellular components of body samples in total or in parts may be regarded as a lysis medium as used herein. Thus lysis mediums as used herein need not contain buffer substances or have buffer capacity.

In certain embodiments of the invention in order to obtain optimal results of the assay, the pH of a lysis medium that can be directly applied to the assay system is around neutral. In further embodiments the pH of the lysis medium is within the range of 4 to 10. In certain other embodiments, the pH is in a range from 5 to 9. In a preferred embodiment, the pH is in a range from 6 to 8. In a more preferred embodiment, the pH is in the range from 6.5 to 7.5.

Examples of lysis media may for example be selected from the compositions given in Table 1.

TABLE 1

| Lysis medium | solubilization of $p16^{INK4a}$ in Western blot | compatibility with Elisa |
|---|---|---|
| Detergents: | | |
| 0.1-1% SDS | + | +/− |
| 0.2-3% SDS | + | <0.5% |
| 0.2-3% DOC | ++ | +/− |
| 0.1-1% n-Octylglycoside | + | yes |
| 0.1-3% Triton x-100% | + | yes |
| 0.1-1% Chaps | + | nd |
| Detergent-Mix: | | |
| RIPA (1% NP40, 0.5% DOC, 0.1% SDS, PBS) 40-100% | ++ | yes |
| SOX (0.5% DOC, 0.5% n-Octylglycoside) 40-100% | + | yes |
| mtm lysis medium (3% Tritonx-100, 0.4% SDS, PBS) | ++ | yes |
| Commerical lysis media: | | |
| Dynal (Dynal, Oslo, Norway) | ++ | yes |
| M-PER/B-PER (Pierce, Rockford, IL) | ++ | yes |
| Miscellaneous: | | |
| 0.5-8M urea in PBS | +++ | Compatible < 2M |
| Lämmli sample buffer | +++ | no |
| 10-80% DMSO | +++ | no |
| 10-80% Formamide | nd | no |
| 50-70% formic acid | ++ | no |
| PBS | +/− | yes |
| Citrate buffer pH 6.0 | +/− | yes |
| 500 mM NaCl in Phosphate buffer | +/− | yes | nd: not determined;
+/−: poor;
+: good;
++: very good;
+++: excellent;

In certain situations, the cyclin-dependent kinase inhibitor $p16^{INK4a}$ can be degraded in the solubilized samples and may thus not be detected. This is particularly true, if the samples are directly transferred to a lysing medium and stored therein for a certain period of time. To prevent degradation, lysis medium may furthermore comprise one or more agents that prevent the degradation of components within the raw samples. Such components may for example comprise enzyme inhibitors such as proteinase inhibitors, RNAse inhibitors, DNAse inhibitors, etc. The inhibitors may e.g. comprise proteinase inhibitors selected from the compositions given in Table 2.

TABLE 2

| Inhibitor | class of inhibited proteinase | concentration | Solubility in water | stability in water | $p16^{INK4a}$ stabilization in mtm Lysis medium |
|---|---|---|---|---|---|
| Aprotinin | Serine | 0.6-2 µg/ml | Very good | good | no |
| Benzamidine | Serine | 0.5-4 mM | good | good | no |
| Bestatin | Aminopeptidases | 1-10 µM | good | good | no |
| Calpeptin | Cysteine | 0.3-1 µM | good | good | no |
| Cystatin | Cysteine | 1 µM | good | good | no |
| E-64 | Cysteine | 1-10 µM | good | good | no |
| EDTA | Metallo | 0.5-5 mM | good | good | no |
| Elastatinal | Serine | 0.5-2 µg/ml | poor | good | no |
| EST | Cysteine | 20-50 µg/ml | bad | poor | no |
| Fetal calf serum | all classes | 10% | good | good | yes |
| Leupeptin | Serine/Cysteine | 10-100 µM | good | good | no |
| a2-Macroglobulin | all classes | 1 µM | good | good | no |
| NCO-700 | Cysteine | 0.5-100 mM | poor | poor | no |
| Pefabloc = AEBSF | Serine | 0.2-10 µM | good | very poor | yes |
| Pepstatin A | Aspartic | 1 µM | bad | poor | no |
| PMSF | Serine | 0.2-10 µM | bad | very poor | yes |
| o-Phenanthroline | Metallo | 1-10 mM | bad | poor | no |

DNase and RNase inhibitors are known to those of skill in the art and may be applied under suitable condition for use in a lysis medium according to the present invention.

For stabilization purpose, the lysis medium may also comprise bulk protein (e.g. albumin such as bovine serum albumin or calf serum albumin or other bulk proteins) to compete in degradation with the sample proteins. The bulk proteins may e.g. be present in combination with proteinase inhibitors or may be added instead of proteinase inhibitors. In one embodiment, the solvent may be selected to be compatible with the assay (e.g. ELISA) performance, so that solubilized samples may directly be applied to the assay.

In some embodiments of the present invention, the lysis medium may be tailored in order to enable for the setting of a specific cut-off value.

In certain embodiments of the invention the kit may be provided as in-vitro diagnostic device. An in-vitro diagnostic device is a kit as defined above, that is intended for assessment of diagnosis of a medically relevant condition from human or animal body samples. In certain embodiments of the invention an in-vitro diagnostic device shall be any device that falls in the scope of the definition of in-vitro diagnostic medical device as given in the directive 98/79 EC under Article 1 (b):

'in vitro diagnostic medical device' means any medical device which is a reagent product, calibrator, control material, kit, instrument, apparatus, equipment, or system, whether used alone or in combination, intended by the manufacturer to be used in vitro for the examination of specimens, including blood and tissue donations, derived from the human body, solely or principally for the purpose of providing information conceding a physiological or pathological state; or concerning a congenital abnormally; or to determine the safety and compatibility with potential recipients; or to monitor therapeutic measures.

In vitro diagnostic device shall also apply to U.S. Class I IVD and generally to in-vitro diagnostic devices that are provided without Claims regarding their diagnostic performance. Therefore also any kind of ASR or the like shall be understood to be an in-vitro diagnostic device as used herein. In one embodiment of the present invention the in-vitro diagnostic device is characterized by solid phase fixed detection reagents specific for a cyclin-dependent kinase inhibitor. In one embodiment, the detection reagents are specific for cyclin-dependent kinase inhibitor $p16^{INK4a}$.

In the art, there are some in-vitro diagnostic devices employing reagents for the detection of cyclin-dependent kinase inhibitor $p16^{INK4a}$ in histological or cytological specimens. These in-vitro diagnostic devices are cell-based detection devices that detect the $p16^{INK4a}$ antigen in cells or tissues, not in solubilized samples.

Cyclin dependent kinase inhibitors such as $p16^{INK4a}$ being intracellular antigens, may only be accessible to detection reagents in solution after permeabilization of cells. Thus, the in-vitro diagnostic application of reagents for detection of cyclin-dependent kinase inhibitor $p16^{INK4a}$ known in the art excludes the fixation of the detection reagents to a solid phase. The art have not taught the design of test kits or in-vitro diagnostics containing $p16^{INK4a}$-fixed solid phase detection reagents. An approach for assessing diagnosis on the basis of solubilized samples seemed not viable from the art and has not been suggested before.

It is thus an aspect of the present invention to provide an in-vitro diagnostic device comprising probes directed against cyclin-dependent kinase inhibitors fixed to a solid phase allowing assessment of diagnosis of carcinomas and their precursor lesions in a solubilized sample. In certain embodiments of the present invention, the probes may e.g. comprise nucleic acids, antibodies or fragments thereof directed against $p14^{ARF}$ or $p16^{INK4a}$ protein. It is an advantage of the in-vitro diagnostic devices of the present invention to allow for easy and economic assessment of diagnosis of cancers and their precursor lesions. The test may be suited for screening purposes as well as for diagnostic purposes and may be applied in primary diagnosis as well as in monitoring of disease course. The in-vitro diagnostic devices may in certain embodiments be applicable for use in clinical laboratories, for point of care testing or even for self testing.

The in-vitro diagnostic devices comprising solid phase fixed reagents for the detection of cyclin-dependent kinase inhibitors may be useful for the detection of various different cancer-entities and their respective precursor lesions. The in-vitro diagnostic devices may be applied for analysis of any kind of lysed body samples.

The probes can be fixed to the solid phase via direct fixation or via indirect fixation. Direct fixation can be done by covalent or non-covalent binding or association to surfaces. Indirect fixation can be done through binding of the antibody to agents which themselves are directly fixed to solid phases. Such agents may comprise antibodies or other binding agents like avidin, streptavidin, biotin, digioxingenin or the like.

The in-vitro diagnostic devices envisaged in the invention are selected from the group consisting of
  a. an ELISA device comprising antibodies directed against cyclin-dependent kinase inhibitor fixed to ELISA plates, ELISA stripes or ELISA wells;
  b. a lateral flow test device, comprising antibodies directed against cyclin-dependent kinase inhibitor fixed to test strips, colloidal gold particles or latex particles;
  c. a flow through assay device, comprising antibodies directed against cyclin-dependent kinase inhibitor fixed to a porous member, or to the surface of capillaries;
  d. a latex agglutination assay device, comprising antibodies directed against cyclin-dependent kinase inhibitor fixed to latex particles; and
  e. an immunoassay device, comprising antibodies directed against cyclin-dependent kinase inhibitor fixed to beads, membranes, or microspheres.

The ELISA devices may be of any kind known to those of skill in the art. These devices comprise devices for sandwich ELISA formats, for competitive ELISA formats and any other ELISA formats.

In one embodiment of the present invention the in-vitro diagnostic device comprises a lysis medium for solubilization of the sample. In a further embodiment of the invention the in-vitro diagnostic device comprises reagents for detection of one specific cyclin-dependent kinase inhibitor fixed to solid phases and no detection reagents of other specificities fixed to solid phases.

Lateral flow assay devices for use as an in-vitro diagnostic device according to the present invention are any lateral flow assay devices employing at least one reagent binding to cyclin-dependent kinase inhibitors fixed to a solid phase. Such devices may employ various mechanisms for visualization of the test result. In certain embodiments, the tests may employ secondary detection reagents directed against cyclin-dependent kinase inhibitors or another components participating in the test coupled to detectable moieties. The detectable moieties may comprise colloidal gold, (colored) latex particles and others.

Flow through assay devices for use in the present invention may comprise devices based on capillaries or on porous members (such as membranes, beads or other three dimensional arrangements of porous substances). Depending on the embodiment the size of pores or capillaries need to adjusted to ensure optimal flow conditions.

A further aspect of the present invention is the use of a solid phase to which detection reagents or probes directed against cyclin dependent kinase inhibitors are fixed or adhere for the manufacture of a test kit or of an in-vitro diagnostic device or for the manufacture of a kit according to the present invention. In certain embodiments of the invention the probes are antibodies or fragments thereof. In further embodiments the probes are oligonucleotides.

The solid phases that may be used for the manufacture of a test kit or of an in-vitro diagnostic device are described above and comprise any suitable solid phase. In certain embodiments the solid phases are membranes, porous member, planar surfaces, multiwell plates (with planar or non-planar surface), colloids, particles and others. All solid phases to which the probes for detection of cyclin-dependent kinase inhibitors may be fixed, may be used for the manufacture of the kits and in-vitro diagnostic devices according to the present invention. Manufacture of such kit according to the present invention may comprise any action suited to provide a finished in-vitro diagnostic device. These actions comprise all manufacturing activities but also repackaging, assembling of single components, re-labeling etc.

It is one aspect of the present invention to provide a method for development of kits and in-vitro diagnostic devices for diagnosis of medically relevant conditions from solubilized body samples, wherein the development is performed using body samples provided as preserved cells in a cell-preservation medium and wherein the preserved cells are intended and prepared for use in cytological examination processes such as Liquid Based Cytology processes. The samples intended for Liquid Based Cytology processes (in the following denominated as LBC samples) are solubilized in an appropriate lysis medium and are used for development activities of kits and in-vitro diagnostic devices for detection of medically relevant conditions from solubilized body samples on the basis of biochemical non-cell-based analysis.

According to the present invention the use of LBC samples for the assessment of diagnosis or for development of kits and in-vitro diagnostic devices may for example provide an accurate and comparable way to provide cytological information for the biochemical non-cell based testing. This may be achieved by employment of normalization of the sample with respect to information obtainable from a cytological specimen prepared out of the same LBC sample. Biochemical normalizaton with respect to markers indicative for the presence or absence of cells or cell types is omissible in such methods. The advantage of using LBC samples in this respect is that the cytologically cell based information is direct related to the homogeineuus LBC specimen and thus provides valuable accurate information for use in the evaluation of the biochemical non-cell based test results.

In the art the filed of application of LBC samples is to enable for improved morphological evaluation of cytology specimens. The field of application of the LBC samples is therefore classically indicated only for cytology. According to the present invention the use of LBC samples as a source for biochemical non-cell based determination of protein levels in solubilized specimens provides the opportunity that the results of the biochemical non-cell based testing may be directly compared to a cytological specimen. The protein based biochemical analysis in this respect may serve as a e.g. pre-testing or to provide further information or even to confirm a cytologically equivocal result In further embodiments the information obtained from the biochemical non-cell based testing may be for the design of the cytological procedures to be applied.

One advantage of such method for development of products is that the same specimen on which the diagnosis for an individual is assessed may be used for assessment of the biochemically based result. Thus comparability of the biochemical result to the diagnosis is ensured.

LBC samples as used in the context of the present invention are any cell samples that are preserved in a standard sample collection, storage or transportation medium, known to those of skill in the art such as e.g. commercially available preservation media (formalin solution, Cytyc "PreservCyt" or "CytoLyt", Digene "Universal Collection Medium", Tripath Imaging "Cytorich", etc.). LBC samples accordingly comprise cell samples in any suitable cell preservation medium that may contain a mixture of one or more selected from a group comprising alcohols, aldehydes, ketones, acids, metal-ions or sublimates, ethers etc. for preservation of cellular components. Alcohols include methanol, ethanol, (n- or i-) propanol, (n-, i- or t-) butanol or higher branched or unbranched alcohols. Aldehydes include formaldehyde, acetaldehyde, glutaraldehyde, etc. Ketones such as Acetone may be used. Acids for use in standard sample media include organic acids (acetic acid, trichloro-acetic acid, salicylic acid, picric acid) or inorganic acids such as e.g. chromic acid.

Standard sample solutions may comprise metals such as silver, copper, chromium, mercury, osmium, uranium. Solutions of salts such as uranyl-acetate, potassiumbichromate, ammonium sulfate, etc. may be components of preservative media.

LBC samples may be samples of any kind of cells taken for various diagnostic purposes. Currently LBC samples with respect to diagnostics in human healthcare are prepared from any body regions where cytological and/or microbiological testing procedures are indicated or seem to be reasonable. It is believed that for a variety of cytologic specimens LBC samples provide a way that minimizes cell loss and preserves morphologic detail. LBC samples according to the present invention therefore comprise samples obtained as Fine Needle Aspirates. Fine Needle Aspirates may comprise specimens from various sources such as e.g. from breast, thyroid (e.g. from nodules), kidneys, pancreas, prostate, lung, lymph nodes, pleura, neck masses, ovaries, synovia, tumor masses etc. LBC samples may furthermore be prepared using body fluids. Suitable body fluids comprise a large range of fluids obtainable from the human or animal body comprising but not limited to e.g. ascites, liquor cerebrospinalis, pus or effusions. Effusions wherever in the body they appear may be subjected to LBC. Some examples for effusions are pericardial, pleural, synovial and abdominal effusions. Body fluids to which LBC may be applied comprise further more e.g. the fluids present in some tumors or cysts such as e.g. breast cysts, ovary cysts or others. Samples obtainable in liquid form from the body comprise furthermore mucous specimens such as e.g. sputum. LBC is widely applied to any kind of exfoliative cytological specimen. Such exfoliative cytological specimens are obtainable by various methods such as e.g. by any by kind of swab, brushing, scrape, smear etc. Also specimens such as washes, lavages etc. from any body region shall be understood to be exfoliative cytological specimens. Washes and lavages may be obtained from a wide range of body regions including but not limited to mucosal epthelia, the skin, any inner or outer body epithelium or the like. Mucocal epithelia may be e.g. those epithelia of the gastrointestinal tract, of the urinary system, of the anogenital tract, of the respiratory tract, of the rectum, the urethra, the cervix, the vagina, the vulva the oral cavity, the endometrial cavity etc. The whole range of exfoliative cytological specimens may be subjected for LBC methods.

Kits as used in the context of the present invention are compositions of components provided for performance of an analytical testing procedure. The kit may comprise all or some of the reagents and materials necessary for proper performance of the test. Furthermore the kit may in certain embodiments of the invention comprise instructions for an appropriate application of the kit components including e.g. an exemplary testing protocol, warnings and hazard information and further accessory information for the user of the kit.

An in-vitro diagnostic device is a kit as defined above, that is intended for assessment of diagnosis of a medically relevant condition from human or animal body samples. In certain embodiments of the invention an in-vitro diagnostic device shall be any device that falls in the scope of the definition of in-vitro diagnostic medical device as given in the directive 98/79 EC under Article 1 (b):

'In vitro diagnostic medical device' means any medical device which is a reagent product, calibrator, control material, kit, instrument, apparatus, equipment or system, whether used alone or in combination, intended by the manufacturer to be used in vitro for the examination of specimens, including blood and tissue donations, derived from the human body, solely or principally for the purpose of providing information concerning a physiological or pathological state; or concerning a congenital abnormality; or to determine the safety and compatibility with potential recipients; or to monitor therapeutic measures.

In vitro diagnostic device shall also apply to U.S. Class I IVD and generally to in-vitro diagnostic devices that are provided without Claims regarding their diagnostic performance. Therefore also any kind of ASR or the like shall be understood to be an in-vitro diagnostic device as used herein. In certain embodiments of the present invention the test kits and in-vitro diagnostic devices to which the methods for development disclosed herein apply are test kits and in-vitro diagnostic devices for protein or peptide based detection of molecular markers.

The testing procedures for which the kits and in-vitro diagnostic devices under development shall be applied according to the present invention include detecting the levels of marker molecules characteristic for medically relevant conditions in the test sample on the basis of biochemical non-cell-based analysis. The markers suitable for these testing procedures according to the present invention may be of various origin. The expression pattern of a marker, that is suitable for the detection of medically relevant conditions in question, may be dependent on the proliferative status of cells, on the differentiation status, on the cell type or on the organism. Examples for appropriate markers are set forth below.

The term diagnosis as used with respect to the kits and in-vitro diagnostic devices under development herein generally comprises any kind of assessment of the presence of absence of a medically relevant condition. Diagnosis thus comprises processes such as screening for the predisposition for a medically relevant condition, screening for the precursor of a medically relevant condition, screening for a medically relevant condition, clinical or pathological diagnosis of a medically relevant condition, etc. Diagnosis or assessment of diagnosis as used herein may furthermore comprise assessment of prognosis or provision of information for stratification of patient therapy on the basis of the biochemical non-cell based testing. Diagnosis of medically relevant conditions as used herein may comprise examination of any condition, that is detectable on a cytological, histological, biochemical or molecular biological level, that may be useful in respect to the human health and/or body. Such examinations may comprise e.g. medically diagnostic methods and research studies in life sciences. In one embodiment of the invention, the method is used for diagnosis of medically relevant conditions such as e.g. diseases. Such diseases may for example comprise disorders characterized by non-wild type proliferation of cells or tissues.

In one embodiment, the diagnosis pertains to diagnosis of neoplastic disorders and their precursor stages, to monitoring of the disease course in neoplastic disorders, to assessment of prognosis of neoplastic disorders and to detection of disseminated tumor cells e.g. in the course of minimal residual disease diagnosis. The method according to the present invention may for example be used in the course of clinical or pathological diagnosis of cancers and their precursor stages or in routine screening tests as performed for particular neoplastic disorders such as for example for examination of swabs e.g. in screening tests for cervical lesions, of bronchial lavages for lung cancer or of stool for lesions of the gastrointestinal tract, e.g. colorectal lesions.

The method of development of kits and in-vitro diagnostic devices according to the present invention is applicable to kits and in-vitro diagnostic devices for the detection and diagnosis of all kinds of medically relevant conditions.

Medically relevant conditions as used according to the present invention may for example be compositions of tissues, body fluids, secretions, washes or swabs. Such conditions may for example comprise the cellular composition of body fluids, such as the composition of blood, the composition of liquor cerebrospinalis or the composition of semen. In this context the compositions shall be for example the presence or absence of particular cell types (e.g. pathogens, such as, viruses etc., preneoplastic, neoplastic and/or dysplastic cells etc.), the presence or absence of differentiation patterns of particular cell types, the total number of a particular cell types (e.g. erythrocytes, leucocytes, sperm, etc.), the total number of all cells of any cell types or the fraction of cells of particular other characteristics present or absent in the sample.

Furthermore, medically relevant conditions may also comprise disorders related to cells, or tissues. The conditions to be diagnosed may comprise parameters related to cells in cytological or histological tissue samples. The conditions may comprise a differentiation pattern of cells in a Ussue sample, such as surgical resection samples, biopsies, swabs, lavages etc. Such conditions may comprise e.g. congenital disorders, inflammatory disorders, mechanical disorders, traumatic disorders, vascular disorders, degenerative disorders, growth disorders, benign neoplasms, malignant neoplasms. Another aspect of the conditions according to the present invention may comprise conditions characterized by the presence or absence of proliferative characteristics. Conditions characterized by the presence or absence of proliferative characteristics may be for example cell proliferative disorders.

Cell proliferative disorders according to the present invention comprise diseases characterized by abnormal growth properties of cells or tissues compared to the growth properties of normal control cells or tissues. The growth of the cells or tissues may be for example abnormally accelerated, decelerated or may be regulated abnormally. Abnormal regulation as used above may comprise any form of presence or absence of non wild-type responses of the cells or tissues to naturally occurring growth regulating influences. The abnormalities in growth of the cells or tissues may be for example neoplastic or hyperplastic.

In one embodiment, the cell proliferative disorders are neoplastic disorders such as tumors. Tumors may comprise tumors of the head and the neck tumors of the respiratory tract, tumors of the anogenital tract, tumors of the gastrointestinal tract, tumors of the urinary system, tumors of the reproductive system, tumors of the endocrine system, tumors of the central and peripheral nervous system, tumors of the skin and its appendages, tumors of the soft tissues and bones, tumors of the lymphopoietic and hematopoietic system, etc. Tumors may comprise for example neoplasms such as benign and malignant tumors, carcinomas, sarcomas, leukemias, lymphomas or dysplasias. In a particular embodiment, the tumor is for example cancer of the head and the neck, cancer of the respiratory tract, cancer of the anogenital tract, cancer of the gastrointestinal tract, cancer of the skin and its appendages, cancer of the central and peripheral nervous system, cancer of the urinary system, cancer of the reproductive system, cancer of the endocrine system, cancer of the soft tissues and bone, cancer of the hematopoietic and lymphopoietic system.

Tumors of the anogenital tract may comprise cancer of the perineal and the scrotal skin, cervical cancer, cancer of the vulva, cancer of the vagina, cancer of the penis, cancer of the anus, etc. Cervical cancer may comprise squamous lesions, glandular lesions or other epithelial tumors. Squamous lesions comprise, e.g., cervical intraepithelial neoplasias (mild, moderate and severe dysplasia), carcinoma in-situ, squamous cell carcinoma (e.g., keratinizing, nonkeratinizing, verrucous, warty, papillary, lymphoepithelioma-like). Glandular lesions may comprise atypical hyperplasias, adenocarcinoma in-situ, andenocarcinoma (such as, e.g., mucinous, endometrioid, clear cell, adenoma malignum, papillary, serous or mesonephric adenocarcinoma). Other epithelial tumors may comprise adenosquamous carcinoma, glassy cell carcinoma, adenoid cystic carcinoma, adenoid basal carcinoma, carcinoid tumor, small cell carcinoma and undifferentiated carcinoma. For more detailed information, confer "Kurman, R., Norris, H., et al., Tumors of the Cervix, Vagina, and Vulva, Atlas of Tumor Pathology, 1992, AFIP," the contents of which shall be incorporated herein by reference.

Gastrointestinal tumors may comprise colon cancer, cancer of the colon ascendens, of the colon descendens, of the colon transversum, of the sigmoidum, of the rectum, cancer of the small intestine, cancer of the jejunum, cancer of the duodenum, gastric cancer, oesophageal cancer, liver cancer, cancer of the bile, cancer of the bilary system, pancreatic cancer, etc. A comprehensive overview over gastrointestinal lesions is given in "Hamilton Sr, Aaltonen L A (Eds.): World Health Organization Classification of Tumours, Pathology and Genetics of Tumors of the Digestive System, IARC Press: Lyon 2000," which shall be incorporated herein by reference.

Tumors of the respiratory tract may comprise any malignant condition of the respiratory tract such as, e.g., cancer of the lung, the alveoles, the bronchioles, the bronchial tree and the broncus, the nasopharyngeal space, the oral cavity, the pharynx, the nasal cavity and the paranasal sinus. Lung cancer such as small cell lung cancer, non-small cell lung cancer, squamous cell lung carcinoma, small cell lung carcinoma, adenocarcinoma of the lung, large cell lung carcinoma, adeno-squamous lung carcinoma, carcinoid tumor of the lung, broncheal gland tumor or (malignant) mesothelioma. An overview over tumors of the respiratory tract may be found in Colby T V, et al.: Tumors of the Lower RespiratoryTract, Atlas of Tumor Pathology, Third Series, Fascicle 13, AFIP: Washington 1995," which shall be incorporated herein by reference.

Tumors of the urinary system may comprise bladder cancer, cancer of the kidney, renal pelvis, cancer of the ureters and cancer of the urethra, etc. Tumors of the reproductive system may comprise cancer and precursory stages thereof of the ovary, the uterus, the testis, the prostate, the epididymis, etc.

In all cases, the methods for which the kits and in-vitro diagnostic devices under developed by a method according to the present invention also apply to precursor stages of the lesions, tumors or cancers.

In one embodiment, the method pertains to the detection of disseminated tumor cells or metastases.

In one embodiment of the invention, the cancer is e.g. cervical cancer, colon cancer, gastric cancer, breast cancer, bladder cancer, lung cancer, cancer of the oral cavity etc.

Development as used in the context of the present invention shall pertain to all design and development activities performed for enabling a manufacturer for controlled production of a finished kit or in-vitro diagnostic device intended for commercial distribution or sale of said kit or in-vitro diagnostic device. Development of kits and in-vitro diagnostic devices as used in the context of the present invention accordingly shall pertain to all activities in connection with the design and development, design- and development-verification, design- and development-validation, assessment of performance data, assessment of safety and effectiveness data of kits and in-vitro diagnostic devices. In one embodiment development shall pertain to the testing of design- and development-outputs of kits and in-vitro diagnostic devices for suitability regarding the proposed intended use. Intended use in this respect shall be understood as the detection or diagnostic purposes for which the kit or in-vitro diagnostic device shall be applied.

The kits and in-vitro diagnostic devices developed according to a method as disclosed herein are characterized in that the detection of the marker molecules characteristic for medically relevant conditions is performed on the basis of biochemical non-cell-based analysis. Biochemical non-cell-based analysis as used in the context of the present invention shall refer to all methods where an analyte or a marker moiecuie is detected in a solution, wherein no information on cellular morphology or on tissue architecture is used for assessment of diagnosis. (Cells and tissue remnants need not necessarily be absent from such solution). Said biochemical non-cell-based analysis is founded on information obtained from the detection of the presence or absence of one or more marker molecules in the solution under investigation or from the detection of the levels of one or more marker molecules in the solution under investigation. In certain embodiments of the present invention the kits and in-vitro diagnostic devices are designed to detect only one single marker molecule. In further embodiments of the present invention the kits and in-vitro diagnostic devices are designed to detect a set of marker molecules. Generally the method of development as disclosed herein may be applied to several types of kit and in-vitro diagnostic devices. Description of different embodiments of kits and in-vitro diagnostic devices is given above.

The detection of said marker molecules in the course of a biochemical non-cell-based analysis may be carried out in solution or using reagents fixed to a solid phase. In certain embodiments of the present invention the detection of the marker molecules is performed from a solution of dissolved body samples. Therefore detection may be carried out in solution or using reagents fixed to a solid phase. A solid phase as used in the context of the present invention may comprise various embodiments of solid substances such as planar surfaces, particles (including micro-, nano-parucles or even smaller particles). In certain embodiments particles may be provided as beads, colloids or the like. The fixation of reagents to the solid phase in a test kit or an in-vitro diagnostic device may be effected via direct fixation or via indirect fixation. Direct fixation may e.g. be effected by covalent or non-covalent binding or association to surfaces. Indirect fixation may be effected through binding of the reagents (e.g. antibodies, probes etc.) to agents which themselves are directly fixed to solid phases. Such agents may comprise antibodies or other binding agents like streptavidin, biotin or the like. The detection of one or more molecular markers may be performed in a single reaction mixture or in two or more separate reaction mixtures. The detection reactions for several marker molecules may for example be performed simultaneously in mult-well reaction vessels or as the case may be on one single or two or more separate test strips. The markers characteristic for the cell proliferative disorders may be detected using reagents that specifically recognise these molecules. The detection reaction in case more than one marker are to be detected may comprise one or more further reactions with detecting agents either recognizing the initial marker molecules or preferably recognizing the prior molecules (e.g. primary antibodies) used to recognize the initial markers. The detection reaction further may comprise a reporter reaction indicating the level of the markers characteristic for cell proliferative disorders.

Marker molecules as used in the context of the present invention shall all times refer to marker molecules characteristic for medically relevant conditions. The terms "marker molecule" or "marker molecule characteristic for medically relevant conditions" in all their grammatical forms as used in the context of the present invention refers to nucleic acid as well as polypeptide molecules. Such marker molecules thus comprises e.g. RNA (mRNA, hnRNA, etc.), DNA (cDNA, genomic DNA, etc.), proteins, polypeptides, proteoglycans, glycoproteins and the respective fragments of these molecules.

A level of a marker molecule as used herein refers to a semiquantitative as well as a quantitative value regarding the amount of the respective marker present in a sample. A quantitative value may e.g. be represented in terms of a concentration. A semiquantitative value may be expressed in terms of a scale of levels e.g. undetectable levels, low levels, intermediate levels, high levels or any other suitable mode. The level of a marker may also be represented in terms of a dependent parameter such as the intensity of a signal generated in an assay format in response to the presence of a marker molecule.

A probe for the detection of the marker molecules as used in the context of the present invention shall be any molecule, that specifically binds to said marker molecules. The probe may for example be an antigen binding agent such as antibodies (monoclonal or polyclonal), antibody fragments or artificial molecules comprising antigen binding epitopes, DNA or RNA binding molecules such as proteins or nucleic acids. Nucleic acids binding to other nucleic acids may for example be peptide nucleic acids (PNAs) or oligonucleotides (RNA, DNA, PNA, artificial nucleic acids, etc.) for detection purposes or primers.

A molecule is said to recognize another molecule if it specifically interacts with that molecule. Specific interaction may for example be specific binding to or of the other molecule.

The reporter reaction may be for example a reaction producing a colored compound. In one embodiment of the present invention the reporter substances correlated to the particular markers develop different colors. In another embodiment, the normalization marker specific reporter may be a molecule quenching the signal produced by the reporter molecule specific for the marker, characteristic for the medically relevant condition, in dependence on the level of the normalization marker present in the sample. In yet another embodiment the reporter reactions may produce fluorescent dyes with differing wavelength characteristics. In a further embodiment of the present invention the reporter reaction may comprise light emitting reactions with different wavelength characteristics for the reporter substances specific for either marker to be detected. In another embodiment of the present invention the reporter reaction may comprise the emission of radioactive radiation and additional methods for visualizing or quantifying the radiation. In one embodiment, the different marker molecules may be recognized by agents, that bear radio-nuclides emitting radiation with different energetic properties, so that the signals referring to marker molecules could be distinguished.

Applicable formats for the detection reactions applied in the kits and in-vitro diagnostic devices according to the present invention may be blotting techniques, such as Western-Blot, Southern-blot, Northern-blot. The blotting techniques are known to those of ordinary skill in the art and may be performed for example as electro-blots, semidry-blots, vacuum-blots or dot-blots. Furthermore immunological methods for detection of molecules may be applied, such as for example immunoprecipitation or immunological assays, such as EIA, ELISA, RIA, lateral flow assays, flow through assays, immunochromatographic strips, etc. Immunoassays for use in the invention may comprise competitive as well as non-competitive immunoassays.

In certain embodiments of kits and in-vitro diagnostic devices developed according to the method of the present invention immunochemical or nucleic acid based testing may be performed using a testing device for clinical laboratories. Such testing device may comprise any device suitable for immunochemical or nucleic acid based testing including any format such as e.g. Point of care testing devices as well as bench top or laboratory devices. The devices may be e.g. provided as open or closed platform systems. The system may be based on any suitable methodology such as e.g. employing microtiter plates, multiwell plates, flow through or lateral flow systems, microchip or array based systems or bead or membrane based systems. The detection methods employed may comprise any methods known to those of skill in the art useful for immunochemical or nucleic acids based detection reactions. Such detection systems may be e.g. luminescence systems (electroluminescence, bioluminescence, photoluminescence, radioluminescence, chemiluminescence, electrochemoluminescence), fluorescence based systems, conductivity based detection systems, radiation (light, UV, X-ray, gamma etc.) or any other known method.

The method for detection of the level of the marker molecules, for which the kits and in-vitro diagnostic devices shall be designed and developed according to the methods disclosed herein, is in one embodiment of the present invention any method, which is suited to detect even very small amounts of specific molecules in biological samples. Furthermore any method for detection of the marker molecules irrespective of the sensitivity may be applied. The detection reaction according to the present invention may comprise for example detection reactions on the level of nucleic acids and/or detection reactions on the level of polypeptides. In one embodiment of the invention, the detection of the marker molecules may comprise the detection of particular splicing variants. In another embodiment of the present invention, the detection method may comprise the detection of modifications of marker molecules such as phosphorylation or glycosylation etc of polypeptides or the methylation of nucleic acid molecules in samples.

In certain embodiments of the present invention the detection of the methylation status of nucleic acids of genes such as $p16^{INK4a}$, $p14^{ARF}$, TSLC1, Claudin, pRB, Her-2/Neu, p53, $p21^{CIP1/WAF1}$, $p27^{KIP1}$ or others may be determined. The presence or absence of hypermethylaton or detection of LOH status on the basis of methylation may be indicative of the presence of a medically relevant condition.

In one embodiment of the invention, the kits and in-vitro diagnostic devices are designed in a way that detection of the level of marker molecules is carried out by detection of the level of nucleic acids coding for the marker molecules or fragments thereof present in the sample. The means for detection of nucleic acid molecules are known to those skilled in the art. The procedure for the detection of nucleic acids can for example be carried out by a binding reaction of the molecule to be detected to complementary nucleic acid probes, proteins with binding specificity for the nucleic acids or any other entities specifically recognizing and binding to said nucleic acids. This method can be performed as well in vitro as directly in-situ for example in the course of a detecting staining reaction. Another way of detecting the marker molecules in a sample on the level of nucleic acids performed in the method according to the present invention is an amplification reaction of nucleic acids, which can be carried out in a quantitative manner such as for example the polymerase chain reaction. In one embodiment of the present invention e.g. real time RT PCR may be used to quantify the level of marker RNA in samples of cell proliferative disorders.

In another embodiment of the invention, the kits and in-vitro diagnostic devices are designed in a way that the detection of the level of marker molecules is carried out by determining the level of expression of a protein. The determination of the marker molecules on the protein level may for example be carried out in a reaction comprising a binding agent specific for the detection of the marker molecules. These binding agents may comprise for example antibodies and antigen-binding fragments, bifunctional hybrid antibodies, peptidomimetcs containing minimal antigen-binding epitopes etc. The binding agents may be used in many different detection techniques for example in western-blot, ELISA, RIA, EIA, flow through assay, lateral flow assay, latex-agglutination, immunochromatographic strips or immuno-precipitation. Generally binding agent based detection may be carried out as well in vitro as directly in situ for example in the course of an immunocytochemical staining reaction. Any other method suitable for determining the amount of particular polypeptides in solutions of biological samples can be used according to the present invention.

Methods for the detection of the modified states of nucleic acid molecules and/or polypeptides are known to those of ordinary skill in the art.

Methods for detection of methylaton of nucleic acids are known to those of skill in the art and may comprise for example methods employing chemical pre-treatment of nucleic acids with e.g. sodium bisulphite, permanganate or hydrazine, and subsequent detection of the modification by means of specific restriction endonucleases or by means of specific probes e.g. in the course of an amplification reaction. The detection of methylaton may furthermore be performed using methylation specific restriction endonucleases. Methods for the detection of methylation states in nucleic acids are e.g. disclosed in patent application EP02010272.9, U.S. Pat. No. 5,856,094, W00031294, U.S. Pat. No. 6,331,393 etc. The cited documents are incorporated herein by reference.

Detection of modified states of polypeptides may for example comprise binding agents specifically recognizing modified or unmodified states of polypeptides. Attentively enzymes such as phosphatases or glycosylases may be used to remove modifications in molecules. The presence or absence of modifications can thus be detected by determination of mass or charge of the molecules by means of electrophoresis, chromatography, mass spectrometry etc. prior and subsequent to the incubation with a respective enzyme.

In a further embodiment of the present invention, the kits and in-vitro diagnostic devices are designed in a way that the detection of a series of marker molecules is carried out on the level of polypeptides and simultaneously the detection of a further series of marker molecules and/or of all or some of the same marker molecules is carried out on the level of nucleic acids.

Marker molecules associated with medically relevant cellular conditions may e.g. be molecules which influence and/or reflect the proliferation and/or differentiation characteristics of cells and/or tissues. Such molecules may comprise for example cell cycle regulatory proteins, proteins associated with the DNA replication, transmembrane proteins, receptor proteins, signal transducing proteins, calcium binding proteins, proteins containing DNA-binding domains, metalloproteinases, kinases, kinase inhibitors, chaperones, embryogenesis proteins, heat shock proteins or enzymes which modify other proteins posttranslationally thus regulating their activity, or nucleic acids coding for the named proteins. Also mRNA coding for the named proteins may be marker molecules useful according to the present invention. In one embodiment the marker associated with the cell proliferative disorder may be for example uniquely expressed in cells affected by the disorder, may be not expressed in said cells or may be overexpressed in said cells.

The kits and in-vitro diagnostic devices developed according to a method as disclosed herein comprise one or more marker molecules (proteins as well as nucleic acids) chosen from cell cycle regulatory proteins or nucleic acids encoding the same (e.g. p53, pRb, p14$^{ARF}$), cyclins (e.g. cyclin A, cyclin B, cyclin E), cyclin dependent kinase inhibitors (such as e.g. p13.5, p14, p15$^{INK4b}$, p16$^{INK4a}$, p18$^{INK4c}$, p19$^{INK4d}$, p21$^{WAF1/CIP1}$, p27$^{KIP1}$), tumor associated antigens (e.g. MDM-2, MCM2, MCM5, MCM6, CDC2, CDC6, Id1, osteopontine, GRP, Claudin, CD46 renal dipeptidase, her2/neu, TGFβII receptor), tumor-suppressor genes, HPV associated markers (e.g. derived from HPV genes L1, L2, E1, E2, E4, E5, E6 or E7, etc.), cell surface antigens (e.g. cytokeratins, catenins or others) or the like. In certain embodiments marker molecules detected by the kits and in-vitro diagnostic devices developed according to the method disclosed herein may comprise genes engaged in the DNA replication such as e.g. proteins or nucleic acids of the pre-initiation complex or of the replication fork. Such molecules may e.g. comprise proliferation markers (proteins as well as nucleic acids) such as e.g. helicases, (such as eucaryotic helicase or MCM proteins [MCM2, MCM3, MCM4, MCM5, MCM6, MCM7], protein TP as disclosed in WO0050451 and WO0217947 [also denominated HELAD1, Pomfil2, Uno-53], kinases or phosphatases engaged in the replication process such as e.g. CDC6, CDC7 protein kinase, Dbf4, CDC14 protein phosphatase, CDC45 and MCM10), proteins engaged in the processive replication fork (such as e.g. PCNA or DNA polymerase delta, replication protein A (RPA), replication factor C (RFC), FEN1), molecules necessary for the maintenance of cell proliferation (such as Ki67. Ki-S5 or Ki-S2), etc. Generally the method for development of kits and in-vitro diagnostic devices disclosed herein is suited for kits and in-vitro diagnostic devices based on various marker molecules characteristic for medically relevant conditions. In one embodiment the marker molecules for a medically relevant condition may be a marker for tumors (tumor markers). The marker molecules characteristic for tumors may e.g. be proteins, that are expressed in a non-wild type manner in tumors compared to normal control issue. Non-wild type expression as used herein may comprise increased or decreased levels of expression, or lack of expression, or expression of non-wild type forms of the respective molecules. Expression of non-wild type forms of a protein may comprise expression of mutated forms of proteins, arising by insertion, deletion, substitution, or frameshift mutations or any other known types of mutations in proteins or nucleic acids. In all cases of the expression of non-wild type proteins or non-wild type levels of proteins the proteins, polypeptides or fragments thereof, or nucleic acids encoding these proteins, or polypeptides or fragments of these nucleic acids may be used as molecular markers associated with tumors and may thus be understood under the term "tumor marker" as used in the context of the present invention. Proteins that show non-wild type expression in association with tumors are disclosed for example in the documents WO9904265A2, WO0149716A2, WO0055633A2 and WO0142792A2, which shall be incorporated by reference herein.

In one embodiment of the invention, the marker characteristic for the medically relevant condition may be a cell cycle regulatory protein such as for example a cyclin, a cyclin-dependent kinase or a cyclin-dependent kinase inhibitor. In a further embodiment of the invention the marker characteristic for the medically relevant condition may be a marker associated with a transient or a persistent viral infection. The viral infection may comprise an infection by a human papilloma virus (HPV) such as high risk or low risk HPV. The high risk HPV may comprise HPV subtypes such as e.g. HPV 16, 18, 31, 33, 35, 39, 45, 51, 52, 56 and 58. The markers for HPV infection may e.g. comprise HPV expression products of HPV genes L1, L2, E2, E4, E5, E6 or E7. In a third embodiment of the invention a marker characteristic for a viral infection may be used in combination with any other marker for a medically relevant condition such as e.g. in combination with a cell cycle regulatory protein. Combinations of marker molecules, which may be of special interest with respect to HPV association are e.g. disclosed in WO0208764 which document shall be incorporated herein by reference.

In one embodiment, cell cycle regulatory proteins for use in combination with HPV markers may for example be chosen from a group comprising pRb, p53, p14$^{ARF}$, cyclin-dependent kinase inhibitors. In one special embodiment for example p16$^{INK4a}$ may be used in combination with markers for HPV infection (e.g. L1, L2, E2, E4, E5, E6 or E7).

In certain embodiments of the present invention a detection of the transcript or protein level of HPV genes is performed. In this respect a normalization of the sample employed in the biochemical non-cell based testing to information from the cytological information prepared from the same LBC sample may be of certain advantage. In one embodiment of the present invention a normalization of the sample for use in the biochemical non-cell based testing with respect to the volume of the LBC sample necessary to prepare a ThinPrep™ specimen using the Cytyc™ ThinPrep™ processor is performed. This may enable to yield comparable results respective the quantity of the HPV nucleic acids compared to the cells present in the sample. If such normalization is omitted not correlation of HPV infection to cellularity may be performed.

For the method of detection of medically relevant conditions as disclosed herein principally any marker molecules may be applied for several medically relevant conditions. However certain marker molecules are known to be associated with specific medically relevant conditions. Those of skill in the art know which marker molecules could reasonably be used in a method according to the present invention for the detection of a medically relevant condition in a solubilized body sample. In Table 3 below examples of medically relevant conditions and marker molecules suitable for application in a method according to the present invention are given. The information is intended to exemplify the method as disclosed herein and not to restrict the scope of the invention, which is as stated generally applicable to molecules known to those of skill in the art to be associated with specific medically relevant conditions.

TABLE 3

| Medically relevant condition | Examples of suitable Marker Molecules for a method as disclosed herein | |
|---|---|---|
| | Protein level | Nucleic Acid Level |
| Cervical Carcinoma | $p16^{INK4a}$, $p14^{ARF}$, claudin, $p19^{INK4d}$, Ki67, Cyclin E, Cyclin D, MCM-5, MCM-2, HPV E7, HPV E2, HPV E4, HPV L1, CK18, CD-46, NMP-173, Brn-3, Mn-antigen; | $p16^{INK4a}$, $p14^{ARF}$, claudin, $p19^{INK4d}$, Ki67, Cyclin E, Cyclin D, MCM-5, MCM-2, HPV E7, HPV E6, HPV E2, HPV E4, HPV L1, (any HPV nucleic acid sequence especially hrHPV), NMP-173, Brn-3, Mn-antigen, TSLC-1, PTEN, NY-ESO1, MCM-5, MCM-2, CDC-6, p53, |
| Bladder Cancer | survivin, MCM-5, MCM-2, CDC-6, Her-2/Neu, MMP-2, Cyclin-E, KIAA1096, $p21^{WAF1/CIP1}$, pRB, MDM2, NMP-22 | Her-2/Neu, MMP-2, Cyclin-E, KIAA1096, $p21^{WAF1/CIP1}$, pRB, MDM2, NMP-22 |
| Colorectal Cancer | Claudin, DNAseX, MCM-5, MCM-2, caveolin-1. cathepsin-B, Cyclin D1, Cyclin E, c-myc, TGF-beta, Her-2/Neu | Claudin, DNAseX, MCM-5, MCM-2, caveolin-1. cathepsin-B, Cyclin D1, Cyclin E, c-myc, TGF-beta, Her-2/Neu |
| Small Cell Lung Cancer | $p16^{INK4a}$, GRP, Her-2/Neu, cyclo-oxigenase-2, NSE, CA 15-3 | $p16^{INK4a}$, GRP, Her-2/Neu, cyclo-oxigenase-2, NSE, CA 15-3 |
| Non Small Cell Lung Cancer | NSE, GRP, Cyclin D1, Her-2/Neu, SCC, CEA, CA 19-9 | NSE, GRP, Cyclin D1, Her-2/Neu, SCC, CEA, CA 19-9 |
| Breast Cancer | Cyclin D3, Her-2/Neu, e-cadherin, survivin, cathepsin D | BRCA2, Cyclin D3, Her-2/Neu, e-cadherin, survivin, cathepsin D |
| Inflammation ion various cytological specimens | Leukocyte specific proteins; Granulocyte specific proteins | Leukocyte specific nucleic acids; Granulocyte specific nucleic acids |

The marker molecules for medically relevant conditions according to the present invention may be characteristic for the presence of absence of a medically relevant condition. In one embodiment of the present invention the marker molecules may be characteristic for specific properties of medically relevant conditions. Such characteristics may comprise the progression potential, prognostic information, behavior respective certain therapeutic treatments of the medically relevant condition. The marker molecules characteristic for medically relevant conditions may therefore be marker molecules useful for the determination of prognosis of individuals affected by medically relevant conditions or for stratification of therapy of individuals affected by medically relevant conditions. This may in certain embodiments apply to the determination of presence or absence of the expression of certain marker molecules that are indicative of positive or negative prognosis in specific medically relevant conditions (e.g. expression Level of p16, Her-2/Neu, Brca-2, Claudin or others in breast cancer etc.) Examples of marker molecules that allow to assess prognosis of individuals affected with specific medically relevant conditions are known to those of skill in the art. Any such markers known from cell based cytological or histological procedures may be used in a method according to the present invention. The assessment of prognosis may e.g. be performed during or after primary diagnosis of the medically relevant condition, during or after (surgical) treatment of the medically relevant condition or at any other stage of the history of the respective medically relevant condition. In other embodiments the method according to the present invention may be used for the stratification of treatment of individuals affected with medically relevant conditions. Such stratification may e.g. comprise the selection of certain therapeutic compounds in the sense of Theragnostic procedures (as used e.g. for selection of patients for therapy with Herceptin or the like), selection of patients for chemotherapy, for radiotherapy or for any other decision on the further therapeutic treatment of individuals or generally for the decision on the medical treatment of individuals such as monitoring follow up or the like.

In certain embodiments of the present invention the marker molecules characteristic for medically relevant conditions may be markers for indicative of progression of the medically relevant condition. In certain further embodiments of the present invention the marker molecules characteristic for the progression of medically relevant conditions may be used in combination with marker molecules characteristic for the mere presence of said medically relevant condition.

The development according to the present invention is performed using LBC samples as raw material. In one embodiment of the present invention the kits and in-vitro diagnostic devices developed according to the method disclosed herein are intended for use with any kind of solubilized body sample. In another embodiment of the present invention the kits and in-vitro diagnostic devices developed according to the method disclosed herein are intended for use with LBC samples only. In this case the kit or in-vitro diagnostic device is developed and manufactured for analysis of solubilized LBC samples as an adjunctive or conjunctive test to the cytological analysis or as a stand alone test.

The method for development of kits and in-vitro diagnostic devices according to the present invention is directed to development of kits and in-vitro diagnostic devices for biochemical testing formats. In these testing formats the presence or absence and/or the level of marker molecules in solubilized body samples is detected. Solubilization of the body samples is performed using a suitable lysis medium as detailed above. The development of a kit or in-vitro diagnostic device according to the present invention makes use of LBC samples for design, development, design and development verification, design and development validation. Furthermore a method for development of kits and in-vitro diagnostic devices on the basis of LBC samples as disclosed herein is any method that employs LBC samples for provision of technical documentation and/or of evidence for safety and effectiveness for the purpose of regulatory clearance or approval of the respective kit or in-vitro diagnostic device before the regulatory authorities and regulatory (notified) bodies if applicable. The method of development of kits and in-vitro diagnostic devices as disclosed herein may employ LBC samples in all stages of the design, development, verification, validation, provision of data for regulatory submission and clearance/approval, or may employ LBC samples only in one or some of the named steps of kit or in-vitro diagnostic device design and development. In one embodiment of the invention the method of development of the kits or in-vitro diagnostic devices according to the present invention is a method for design and development of said kits and in-vitro diagnostic devices, wherein the LBC samples are used for design and development verification and/or validation. In another embodiment of the invention the method of development of kits and in-vitro diagnostic devices is a method for provision of data for regulatory submission and clearance/approval of kits and/or in-vitro diagnostic devices before national or regional regulatory authorities and/or national or regional regulatory (notified) bodies, wherein LBC samples are used for the provision of technical data, performance data or safety and effectiveness data regarding the kit or in-vitro diagnostic device. In a further embodiment of the invention the method of development of kits and in-vitro diagnostic devices is a method where the latter methods are combined.

The method for development of kits and in-vitro diagnostic devices as detailed herein makes use of LBC samples in any way that is suitable for gathering data on the performance characteristics of the kit or device under development. Generally LBC samples are used as a source of body samples to be used in the course of the kit or in-vitro diagnostic device development. In one embodiment of the present invention the LBC sample is supplied as a left over specimen, wherein a cytological specimen has been prepared from the LBC sample before, during or after use of parts of the LBC sample for the development method according to the present invention. In another embodiment the LBC sample has been obtained solely for the purpose of use in a method of development according to the present invention. In this case a second and may be third LBC sample or even sample prepared by conventional non thin-layer methods for cytological evaluation may have been obtained before or after the sampling of the respective LBC sample used in the method of development according to the present invention.

Regarding the LBC samples used in the method according to the present invention information regarding the cytological procedures may be present or absent. Such information comprises e.g. the volume of an LBC sample needed for preparation of a suitable thin-layer preparation, information on the cell content of the LBC specimen, information on the adequacy of the LBC specimen or the underlying sampling procedure, information on the diagnostic information assessed on the basis of a cytological specimen, information on the patient disease and diagnosis etc.

In a method according to the present invention the LBC sample obtained is used either in its entirety or only in parts. In certain embodiments of the invention the total volume of an LBC sample is used for the development purpose. In another embodiment the total number of cells contained in the sample is used for the development purpose. In yet another embodiment only a fraction of the total volume or of the total number of cells contained in the original LBC sample is used for the purpose of development.

In a method according to the present invention a normalization of the LBC sample may be applied. In certain embodiments of the invention a normalization of the LBC sample may be applied to ensure the presence of a comparable amount of cells in the development processes performed using the LBC sample. This may be achieved by normalizing the volume of the LBC sample with respect to the volume of said sample necessary for preparation of an appropriate thin-layer specimen. Preparation of the thin-layer specimen may be performed by any suitable method such as e.g. employing ThinPrepxm processor or the like. In this case the volume of the fraction of the LBC sample for employment in the development process according to the present invention may be disregarded. In certain further embodiments the normalization of the LBC sample is performed with respect to the volume of the sample subjected to the testing procedure. In this case the amount of cells present in the fraction of the LBC sample for employment in the development process according to the present invention may be disregarded. Examples for performance of normalization as described herein are given in Examples 4 ff.

A further aspect of the present invention is a method for assessment of diagnosis of medically relevant conditions by biochemical non-cell-based analysis of the presence or absence and or the level of marker molecule in solubilized body samples, wherein the body sample is an LBC sample. In certain embodiments of the invention the method for assessment of diagnosis comprises a normalization of the amount of sample applied for the biochemical non-cell based testing with respect to information accessible from a cytological (e.g. thin-layer) preparation generated from the LBC sample. This information may e.g. be information on the cellularity of the sample. In this respect cellularity shall be understood as the cell content per mL present in the medium. The cellularity may refer to an overall content of cells of whatsoever kind and nature. In other embodiments the term cellularity may refer to the content of specific defined call types in the LBC sample. Such cells may e.g be cells defined by means of source or location (e.g. endocervical cells, ectocervical cells, endometrial cells, cervical cells, vaginal cell) cells defined by proliferation and/or differentiation status (e.g. metaplastic cells, dysplastic cells, HPV infected cells, etc.) or any other defined type of cells.

The method of detection disclosed herein in this respect pertains to detection of marker molecules such as nucleic acids or proteins or peptides and the respective fragments thereof. In certain embodiments the detection of marker molecules is carried out by detection of the presence or absence and or the level of proteins, peptides or fragments thereof in said solubilized samples. The marker molecules that may be applied for this method are disclosed above as "marker molecules characteristic for medically relevant conditions". The method may be applied to any medically relevant condition as defined above. In other embodiments of the invention nucleic acids of marker molecules characteristic for medically relevant conditions are detected. Nucleic acids as used in this respect is defined above in the description of this invention.

The detection of the marker molecules in the methods as disclosed herein refers to any suitable detection methods as defined above. In certain embodiments the detection of proteins and peptides is carried out by means of immunochemical detection.

By means of the present invention, it is possible to diagnose neoplastic disorders such as cancers and their precursor stages early. In particular, precursor stages of cancers can be detected early. It must also be emphasized that it is possible to make a differentiation with respect to benign inflammatory or metaplastic changes of neoplastic disorders. Another characteristic is that the results obtained by a method according to the invention do not rely on subjective evaluation, so that e.g. false-negative results and false-positive results of a Pap test or histological preparations can be reduced or avoided. In addition, the present invention distinguishes itself by rapid and simple handling, so that it can be used for extensive screening measures, particularly also in third-world countries. Thus, the present invention represents an important contribution to today's diagnostics of cancerous diseases.

EXAMPLES

Example 1

Detection of Cervical Intraepithelial Neoplasia in an ELISA Test Format 33 cervical swabs provided in a lysis medium were subjected to ELISA based detection of overexpression of cyclin-dependent kinase inhibitor p16$^{INK4a}$ in solutions prepared from the cells contained in the swabs. The ELISA testing was performed as follows:

(A) Cell Lysis

Cervical swab brushes were given into 15 ml vessels, containing 2 ml of mtm lysis medium (2% Triton X-100, 0.4% SDS, 0.6 mM PMSF in PBS). Cervical cells present in the brush were lysed for at least 20 h. The lysates of the cervical swab samples were then transferred in 2 ml tubes and were centrifuged at 4° C. (15 min at 28.000×g (16.600 rpm Highspeed Centrifuge JEC Multi RF)); Supernatant was transferred to a fresh tube. The Supernatant may be stored at −20° C.

(B) Performing the ELISA

Coating of ELISA-Plates

Stock-solution of p16$^{INK4a}$ specific antibody clone mtm E6H4 was diluted in PBS to give ready-to-use coating solution.

50 µl of the coating solution was added to each well of the ELISA plates.

For coating, the plates were incubated overnight at 4° C.

Coating solution was removed from the ELISA plates and the plates were rinsed using an automated ELISA washer as follows:

7×250 µl washing buffer (0.1% Tween20 (v/v) in PBS)

after removing remnants of the washing buffer, 300 µl blocking buffer (2% BSA in PBS) was added to each well. Plates were incubated for 1 h on a rocking device at ambient temperature.

Incubation with Samples

After removing the blocking buffer, 100 µl of the lysed cell sample was added to each well. Lysates of HeLa-cells were used as positive control;

For purpose of calibration of the test, different concentrations of recombinant p16$^{INK4a}$ protein (0 pg/ml, 50 pg/ml, 100 pg/ml, 200 pg/ml, 400 pg/ml, 800 pg/ml) were included in the test.

Samples were incubated for 1 h at room temperature.

Thereafter washing was performed on an automated ELISA washer as follows:

7×250 µl washing buffer. The remaining buffer was removed.

Incubation with Detection Antibody

Working solution of biotinylated secondary antibody clone mtm D7D7 specific for p16$^{INK4a}$ protein was prepared by dilution of stock solution.

100 µl of working solution was added to each well. After incubation for 1 h at RT, antibody solution was removed and ELISA plates were washed by an automated ELISA washer 7× with 250 µl washing buffer.

Detection

Streptavidin-HRP-polymers (1 mg/ml) were pre-diluted 1:10. (4 µl+36 µl incubation buffer); Final incubation solution was prepared by dilution 1:300 in incubation buffer (0.1% BSA in PBS) to a final concentration of 0.33 µg/ml.

100 µl of this solution were added to each well and incubated for 1 h at RT.

Thereafter, the buffer was removed and the plates were washed manually with 200 µl washing buffer per well 5 times.

Substrate Incubation

TMB-substrate was equilibrated to 25° C. for 1 h in the dark.

100 µl of substrate solution was added to each well.

The ELISA plates were incubated at 25° C. for exactly 15 min in the dark. Then the reaction was stopped by addition of 80 µl 2.5M H2SO4.

Within 5 min. after stopping the reaction, OD 450 nm was determined. After evaluation of the results, each sample returned a value for the OD.

Results of this experiment are given in Table 4. The ELISA results were compared to the diagnostic results of a Papanicolaou test (PAP test, cervical cytology) from the same patients. The cervical cytology were evaluated according to the Munich Classification II (1990). Pap II encompasses benign cells, cervicitis and metaplasia, Pap IV encompasses severe dysplasia and carcinoma in situ. It turned out that samples returning an OD greater than 0.9 in the ELISA correspond to samples, that are classified as dysplastic by the conventional cytological PAP test.

Applying OD 0.9 as threshold for the evaluation of the samples, the ELISA results may be reported as follows:

TABLE 4

| Diagnosis/ELISA results | ELISA positive | ELISA negative |
|---|---|---|
| Pap II | 0 | 30 |
| Pap IV | 3 | 0 |

The ELISA test is positive in all samples (100%) from women having severe dysplasia and is negative in all 30 samples (100%) of women having no dysplasia.

Using the threshold evaluated in these experiments, cytological specimens of 300 patients were tested in the presented ELISA testing format. In this experiments the specimens identified as being dysplastic by cytological examination may also be identified as dysplastic in the ELISA testing format.

The results show, that the quantification of p16$^{INK4a}$ protein in solubilized patient samples allows to detect dysplasias from the samples. The diagnosis in the present example is based on the comparison of the level of p16$^{INK4a}$ determined in a specific patient sample to the level known to be present in normal non-dysplastic samples. The comparison is carried out in the testing format by applying a threshold value for the OD determined in the ELISA above which the sample is to be classified as positive.

Example 2

Detection of Cervical Intraepithelial Neoplasia in an Lateral Flow Test Format

Nine cervical swabs provided in PreservCyt (Cytyc Corporation, Boxborough, Mass.) solution have been subjected to conventional PAP testing and simultaneously to lateral flow based detection of overexpression of cyclin-dependent kinase inhibitor p16$^{INK4a}$ in solutions prepared from the cell suspensions obtained from the swabs. The lateral flow testing was performed as follows:

(A) Cell Lysis 10 ml of the cell suspensions from the individual cervical swab samples provided as PreservCyt™ fixed materials were transferred to a 15 ml reaction vessel. The samples were centrifuged 15 min at ambient temperature at 1500×g (3000 rpm, Heraeus Varifuge, rotor 8074); supernatant was discarded, and remaining methanol allowed to evaporate (15 min at ambient temperature); the pellet was solubilized in 500 µl Lysisbuffer and transferred to a 1.5 ml reaction vessel. The solution was centrifuged at 4° C. (15 min at 28000×g (16600 rpm Microcentrifuge Biofuge fresco)); Supernatant was transferred to a fresh tube. Supernatant may be stored at −20° C.

(B) Performing the Lateral Flow Assay

Applying Capture Antibody to Membrane

Stock solution of p16$^{INK4a}$ specific antibody done mtm E6H4 was diluted in TBS (containing 1% bovine serum albumin) to give ready-to-use spotting solution with a final concentration of 1 mg antibody/ml. The ready-to-use solution was spotted onto nitrocellulose membrane at 30 µl/30 cm. Whatman wicks were attached to one end of the nitrocellulose and dipsticks are dried for 1 hour at 37° C. Then they were allowed to equilibrate at room temperature and cut into 4 mm width dipsticks.

Preparation of Conjugate Solution

Stock-solution of p16$^{INK4a}$ specific antibody clone mtm D7D7, conjugated to colloidal gold (40 nm particle size) was diluted in TBS (containing 1% bovine serum albumin) to give ready-to-use detection antibody solution with a final concentration of 1.0 OD at 520 nm.

Incubation with Samples

Then 20 µl of the lysed cell samples were added to 20 µl ready-to-use detection antibody solution in a microtiter well and mixed. Dipstick, coated with capture antibody clone E6H4 was added to the well, sample was soaked and run to completion. The signal was read while the dipstick is still wet.

Results

In our testing format, 2 samples (samples 1 and 2) classified as PAP IVa by PAP staining and therefore containing dysplastic cells, gave clearly visible purple bands in the area of spotted capture antibody. In contrast, no band was detected for the other 7 samples (samples 3-9), classified as PAP II-III by PAP staining and therefore not containing dysplastic cells.

ELISA was performed by the same protocols given in Example 1. The results are shown in Table 5.

TABLE 5

| Sample | Diagnosis | ELISA OD |
|---|---|---|
| 1 | Pap IVa | 2.209 |
| 2 | PAP IVa | 0.536 |
| 3 | PAP III | 0.067 |
| 4 | PAP II | 0.113 |
| 5 | PAP II | 0.095 |
| 6 | PAP II | 0.284 |
| 7 | PAP II | 0.192 |
| 8 | PAP II | 0.138 |
| 9 | PAP II | 0.07 |

Example 3

Detection of p16$^{INK4a}$ and p14$^{ARF}$ Transcripts by RT-PCR,

Cervical samples from 50 individuals were used for this analysis. For each individual two samples were obtained, one in Universal Collection Medium and one in PreservCyt™ solution. Both samples were obtained during the same examination session. For each of the individuals a diagnosis based on analysis of a cervical thin layer specimen prepared out of the PreservCyt™ solution was available. 20 of the samples included in the present study were chosen to be diagnosed as NILM, 20 samples were chosen to be LSIL and 10 samples were chosen to be HSIL. From all samples the level of transcripts of p16$^{INK4a}$ and of p14$^{ARF}$ have been determined on an mRNA level by RT-PCR according to the following protocol:

For performance of the analysis the cells were pelleted from the UCM and PreservCyt™ solutions by centrifugation. The pellets obtained were directly subjected to the RNA preparation procedure.

The pellet was diluted and resuspended in ready to use RLT Buffer. After adding 70% Ethanol to the homogenised lysat the suspension was mixed by pipetring.

Purification and isolation of RNA was performed using QIAamp Spin-columns according to the directions of the manufacturer.

RNA concentration was determined photometrically at 260 nm. For reverse transcriptase reaction from 100 ng up to 500 ng RNA were used. DNA was degraded by DNase reaction as follows 17.0 µL RNA (6-30 ng/µL)

1.0 µl DNAse I Amp Grade (1 Unit/µl)(Invitrogen)

2.0 µl DNAse Reaction Buffer (10×)(Invitrogen)

20.0 µl total volume

Incubation was performed for 15 Min at 25° C. and the reaction was stopped by adding 2 µl EDTA 25 mM and incubation for 10 Min at 65° C.

cDNA synthesis was performed using the whole volume of the DNase digest using Omniscript reverse transcriptase in the presence of RNAsin.

The reaction was performed for 2 h at 37° C. and subsequently 5 Min at 93° C. Afterwards the mixture was stored at 4° C. This renders a ready to use cDNA solution for the Taqman-PCR (corresponds to a cDNA concentration of about 7-36 ng/5 µl).

For use in RT-PCR the 40 µl cDNA Reaction mixture was diluted with 30 µl RNase-free water to a volume of 70 µl. The primers used were:

```
                                            (SEQ ID NO: 1)
Primer p16INK4a, forward:
5'-CGA ATA GTT ACG GTC GGA GG-3'

(SEQ ID NO: 2)
Primer p16INK4a, reverse.
5'-ACC AGC GTG TCC AGG AAG-3'

(SEQ ID NO: 3)
Primer p14ARF, forward:
5'-CCG CCG CGA GTG AGG GTT-3'

(SEQ ID NO: 4)
Primer p14ARF, reverse.
5'-TGC CCA TCA TCA TGA CCT GGT CT-3'
```

As controls PCR reactions for β-actin and GAPDH were performed using the primers:

```
                                            (SEQ ID NO: 5)
Primer (63) β-Actin, forward:
5'-CCT AAA AGC CAC CCC ACT TCT C-3'
```

-continued

Primer (64) β-Actin, reverse: (SEQ ID NO: 6)
5'-ATG CTA TCA CCT CCC CTG TGT G-3'

Primer GAPDH, forward: (SEQ ID NO: 7)
5'-ACC ACA GTC CAT GCC ATC AC-3'

Primer GAPDH, reverse: (SEQ ID NO: 8)
5'-TCC ACC ACC CTG TTG CTG TA-3'

Each primer was used at a concentration of 300 nmol. The reaction mixture for RT-PCR was composed as follows:

12.5 µl SYBR-Umix
0.25 µl Primer Mix
7.25 µl Wasser für die Molekularbiologie
5.0 µl cDNA solution
25.0 µl total volume The conditions for the 2 Step Real Time PCR are:
$1^{st}$ Step: 50° C. 2 Min, 95° C. 10 Min
$2^{nd}$ Step: 95° C. 15 sec, 60° C. 1 Min 10 sec. 40 Cycles Evaluation of the RT-PCR results was performed by estimation of the degree of overexpression of the $p16^{INK4a}$ transcripts on the basis of the level of transcripts detected in the sample specimens compared to levels of transcripts present in normal tissue or cell specimens. Normalization with respect to the level of housekeeping genes detected in each sample was performed for the levels of $p14^{ARF}$ prior to analysis of overexpression. An overexpression of 0 to 24 times compared to normal tissue was regarded as not relevant. Only levels of overexpression of $p16^{INK4a}$ and $p14^{ARF}$ higher than 24 times were regarded as significantly elevated transcript levels in the samples. It must be noted, that this scheme for evaluation is only one of several equally suitable methods. Those of skill in the art know how the results of RT-PCR may be used to estimate transcript levels and to do correlations to clinical parameters of specimens. The Threshold mentioned in this example is exemplary and may vary depending on conditions.

The values obtained from the UCM specimen of one sample and the corresponding PreservCyt™ specimen gave the same results.

A comparison of the detected transcript level to the diagnosis of the correlated specimen from cytology showed good correlation between elevated transcript levels and presence of cervical lesions diagnosed on the basis of cytological thin-layer specimens.

The correlation was as follows:

TABLE 6

| Level of transcripts of $p16^{INK4a}$ as detected in RT-PCR[expressed as times elevation compared to levels found in normal specimens] | Gene | Cytological Diagnosis | | |
|---|---|---|---|---|
| | | NILM | LSIL | HSIL |
| 0 to 24 times elevated | $p16^{INK4a}$ | 19 | 0 | — |
| | $p14^{ARF}$ | 16 | 3 | — |
| higher than 24 times elevated | $p16^{INK4a}$ | 1 | 20 | 10 |
| | $p14^{ARF}$ | 4 | 17 | 10 |

The experiment shows that a method for detection of transcript level of $p16^{INK4a}$ and $p14^{ARF}$ in lysed cervical samples is suited for assessment of diagnosis of cervical lesions and their precursors. The tested cell preservation solutions turned out to be equally suitable for the disclosed method. The transcript levels of both tested genes may be used for adding in assessment of diagnosis of cervical intraepithelial neoplasia, wherein $p16^{INK4a}$ shows slightly better results than $p14^{ARF}$.

Example 4

Hybrid Capture Analysis of Transcript Levels of $p16^{INK4a}$ and $p14^{ARF}$ in Liquid Based Cytology Samples from Swabs from the Oral Cavity, Sputum and from Cervical Swabs Each 10 LBC samples in PreservCyt™ or CytoLyt™ solution respectively of cervical swabs from individuals with diagnosed HSIL lesion, of sputum from individuals with small cell lung cancer, and of swabs from the oral cavity from individual with cancer of the oral cavity were used for each of the marker molecules in the present example (In total 20 specimens for each cancer entity were included.). For the cervical and oral specimens a hybrid capture analysis for the presence of hrHPV types and of transcripts of $p16^{INK4a}$ and $p14^{ARF}$ was performed. Hybrid capture for hrHPV types was performed using HybridCaptrue hc2 test by Digene Corp. Hybrid capture analysis for the transcripts of the named cyclin-dependent kinase inhibitors was performed as described below.

(A) Cell Lysis

For the present example the amount of the LBC sample was dependent on the cell content of the LBC sample. A thin-Layer specimen of each sample was prepared using a Cytyc ThinPrep™ processor. The mass of the LKBC sample was determined before and after the preparation of the thin-layer specimen. As the ThinPrep™ processor consumes upon each processing only the amount, of sample necessary for a specific cell density on the filter the volume consumed is a measure for the relative cell concentration in the LBC sample. In the present example from each LBC two times the mass consumed for the preparation of the thin-layer specimen by the ThinPrep™ processor was applied for the hybrid capture analysis. (Samples for which the cellularity of the LBC sample was too low have been excluded.)

For performance of the analysis the cells were pelleted from the CytoLyt™ and PreservCyt™ solutions by centrifugation. The pellets obtained were directly subjected to the RNA preparation procedure.

The pellet was diluted and resuspended in ready to use RLT Buffer. After adding 70% Ethanol to the homogenised lysat the suspension was mixed by pipetting.

Purification and isolation of RNA was performed using QIAamp Spin-columns according to the directions of the manufacturer.

For detection of the $p16^{INK4a}$ mRNA a mixture of 40-mer DNA oligonucleotide probes specific for $p16^{INK4a}$ and $p14^{ARF}$ were used. The most suitable probes in the mixture had the following sequences: $p14^{ARF}$:

(SEQ ID NO: 9)
5'-GCT CCG CCA CTC GGG CGC TGC CCA TCA TCA TGA CCT GGT C-3'

(SEQ ID NO: 10)
5'-GCC ACT CGG GCG CTG CCC ATC ATC ATG ACC TGG TCT TCT A-3'

-continued

```
                                                (SEQ ID NO: 11)
5'-TCG GGC GCT GCC CAT CAT CAT GAC CTG GTC TTC TAG
GAA G-3'

(SEQ ID NO: 12)
5'-CGC TGC CCA TCA TCA TGA CCT GGT CTT CTA GGA AGC
GGC T-3'

(SEQ ID NO: 13)
5'-CCC ATC ATC ATG ACC TGG TCT TCT AGG AAG CGG CTG
CTG C-3'

(SEQ ID NO: 14)
5'-CAT CAT CAT GAC CTG GTC TTC TAG GAA GCG GCT GCT
GCC CTA G-3'

(SEQ ID NO: 15)
5'-TGC CCA TCA TCA TGA CCT GGT CTT CTA GGA AG-3'

(SEQ ID NO: 16)
5'-ATC ATC ATG ACC TGG TCT TCT AGG AAG CGG CTG CTG
CCC TAG-3'
```

It is advantageous to place the probes on the border between Exon 1β and Exon 2 of the mRNA to ensure that only p14$^{ARF}$ specific mRNA is recognized by the probes (the situation is similar for specific PCR conditions for p16$^{INK4a}$ and p14$^{ARF}$ respectively; primer pairs could be selected to cover the Exon boundary within the amplificat.). Any other probes specifically recognizing p14$^{ARF}$ mRNA may be used similarly. The probes disclosed in this example are used as an example and are not intended to restrict the scope of the invention. Probe sequence comprising the above sequences or fragments thereof may similarly be used for a method as disclosed herein.

For p16$^{INK4a}$ promising probe sequences are the following:

```
                                                (SEQ ID NO: 17)
5'-CTC CGC CAC TCG GGC GCT GCC CAT CAT CAT GAC CTG
GAT CGG-3'

(SEQ ID NO: 18)
5'-ACT CGG GCG CTG CCC ATC ATC ATG ACC TGG ATC GGC
CTC-3'

(SEQ ID NO: 19)
5'-CGG GCG CTG CCC ATC ATC ATG ACC TGG ATC GGC CTC
CGA-3'

(SEQ ID NO: 20)
5'-GCT GCC CAT CAT CAT GAC CTG GAT CGG CCT CCG ACC
GTA A-3'

(SEQ ID NO: 21)
5'-CAT CAT CAT GAC CTG GAT CGG CCT CCG ACC GTA ACT
ATT C-3'

(SEQ ID NO: 22)
5'-ATC ATC ATG ACC TGG ATC GGC CTC CGA CCG TAA CTA
TTC GGT GC-3'

(SEQ ID NO: 23)
5'-AGC AGC TCC GCC ACT CGG GCG CTG CCC ATC ATC ATG
ACC TGG ATC-3'

(SEQ ID NO: 24)
5'-ATC ATC ATG ACC TGG ATC GGC CTC CGA CCG TAA CTA
TTC-3'

(SEQ ID NO: 25)
5'-TCA TCA TGA CCT GGA TCG GCC TCC GAC CGT AAC TAT
TCG GT-3'
```

Similar as to the situation with p14$^{ARF}$ for p16$^{INK4a}$ the probes preferably are places to overlap with the exon boundary of Exon 1α to Exon 2. This provision could ensure that p16$^{INK4a}$ is recognized and no other mRNA transcribed from the INK4 locus. Further more the comments given for the probes to p14$^{ARF}$ apply here mutandis mutatis.

The labeled probe mixture was added to the total cellular RNA extract For hybridization the mixture was incubated at 65° C. for 30 Min.

(B) Performing the ELISA

For the detection of the RNA-DNA hybrids microtiter plates coated with anti-RNA/DNA-hybrid antibodies available from Digene Corp. were used. The hybridization solution was added directly to the microtiter plates and incubated for 1 h at ambient temperature. The plates are washed according to the instructions by the manufacturer. Detection was performed using the secondary anti-RNA/DNA-hybrid antibody and detection reagents provided by Digene Corp.

The hybrid capture assay revealed positive results for p16$^{INK4a}$ for all cervical specimens. This result was in concordance with all cervical specimens being positive for hr HPV by Hybrid Capture. About half of the cancer specimens from the oral cavity was tested as p16$^{INK4a}$ overexpressing. All of these specimens being positive for p16$^{INK4a}$ have been tested for hrHPV by hc2. There was significant correlation between HPV positivity and p16$^{INK4a}$ overexpression in cancer of the oral cavity. For small cell lung cancer p16 could be detected as positive in 8 out of 10 of the tested cases. All results for p16$^{INK4a}$ obtained by the hybrid capture test could be confirmed by immuno-cytochemical analysis of the thin-layer specimens.

For p14$^{ARF}$ the results for cervical samples were comparable to those for p16$^{INK4a}$. For small cell lung cancer only two of the 10 cases under investigation showed positivity for 14$^{AFR}$ in hybrid capture. This result could be confirmed by immuno-cytochemistry. In the LBC samples from the oral cavity p14$^{ARF}$ could be detected in 7 out of 10 cases in concordance with the immuno-cytochemical findings.

The results show that detection of cyclin-dependent kinase inhibitors in a habrid capture testing format from LBC samples may be used for assessment of diagnosis of several cancer entities. The results suggest that the biochemical testing could be used as an adjunct or conjunct testing to a cytological testing.

Example 5

Immunochemical Analysis of Protein Levels of p16$^{INK4a}$, Her-2/Neu and p14$^{ARF}$ in Liquid Based Cytology Samples from Urine, Sputum, Breast Fine-needle Aspirates and from Cervical Swabs 10 cervical swabs with a cytological classification as HSIL, 10 sputum samples with cytologically diagnosed small cell lung cancer, 10 urine samples from individuals with diagnosed bladder tumors and 10 fine needle aspirates from individuals with diagnosed DCIS, all provided in PreservCyt™, medium were subjected to centrifugation of the cells and subsequent solubilization of the cells in a lysis medium. Afterwards ELISA based detection of expression level of cyclin-dependent kinase inhibitor p16$^{INK4a}$, of p14$^{ARF}$ and of HER-2/Neu in solutions prepared from the cells contained in the swabs. The ELISA testing was performed as follows:

(A) Cell Lysis

Each 10 mL of the LBC samples were centrifuged to allow the cells to sediment. The cell pellet is [TIME] dissolved in 700 μl of of mtm lysis buffer lysis medium (2% Triton X-100, 0.4% SDS, 0.6 mM PMSF in PBS) by mixing and incubating for 10 Min at 80° C. The lysates of the LBC samples were then centrifuged at 4° C. (15 min at 28.000× g (16.600 rpm HighspeedCentrifuge JEC Multi RF)); Supernatant was transferred to a fresh tube. The Supernatant may be stored at −20° C.

(B) Performing the ELISA

Coating of ELISA-Plates

For each protein separate ELISA plates were prepared as follows. Stock-solutions of the primary antibodies specific for $p16^{INK4a}$, $p14^{ARF}$ and HER-21Neu were diluted in PBS to give ready-to-use coating solution.

For $p16^{INK4a}$ clone mtm E6H4 was used for coating of ELISA plates. For $p14^{ARF}$ polyclonal antibody directed against $p14^{ARF}$ available from Calbiochem was used. For Her-2/Neu polyclonal antibody from DakoCytomation was used for coating.

50 µl of the coating solution was added to each well of the ELISA plates.

For coating, the plates were incubated overnight at 4° C.

Coating solution was removed from the ELISA plates and the plates were rinsed using an automated ELISA washer as follows:

7×250 µl washing buffer (0.1% Tween20 (v/v) in PBS) after removing remnants of the washing buffer, 300 µl blocking buffer (2% BSA in PBS) was added to each well. Plates were incubated for 1 h on a rocking device at ambient temperature.

Incubation with Samples

After removing the blocking buffer, 100 µl of the lysed cell sample was added to each well.

For purpose of calibration of the test, different concentrations of recombinant proteins (0 pg/ml, 50 pg/ml, 100 pg/ml, 200 pg/ml, 400 pg/ml, 800 pg/ml) were included in each of the tests.

Samples were incubated for 1 h at room temperature.

Thereafter washing was performed on an automated ELISA washer as follows:

7×250 µl washing buffer. The remaining buffer was removed.

Incubation with Detection Antibody

Working solution of biotinylated secondary antibodies specific for the respective proteins were prepared by dilution of stock solution. For $p16^{INK4a}$ mtm clone D7D7 was applied, for $p14^{ARF}$ monoclonal antibody from Calbiochem was applied and for HER-2/Neu monoclonal Antibody from DakoCytomation was used. 100 µl of working solution was added to each well. After incubation for 1 h at RT, antibody solution was removed and ELISA plates were washed by an automated ELISA washer 7× with 250 µl washing buffer.

Detection

Streptavidin-HRP-polymers (1 mg/ml) were pre-diluted 1:10. (4 µl+36 µl incubation buffer); Final incubation solution was prepared by dilution 1:300 in incubation buffer (0.1% BSA in PBS) to a final concentration of 0.33 µg/ml.

100 µl of this solution were added to each well and incubated for 1 h at RT.

Thereafter, the buffer was removed and the plates were washed manually with 200 pij washing buffer per well 5 times.

Substrate Incubation

TMB-substrate was equilibrated to 25° C. for 1 h in the dark.

100 µl of substrate solution was added to each well.

The ELISA plates were incubated at 25° C. for exactly 15 min in the dark. Then the reaction was stopped by addition of 80 µl 2.5M $H_2SO_4$.

Within 5 min. after stopping the reaction, OD 450 nm was determined. After evaluation of the results, each sample returned a value for the OD. For each antibody a threshold OD was determined using the value seen for background.

The ELISA results were compared to the diagnostic results of the cytological evaluation of the specimens from the same individuals. The results are as follows in Table 6:

TABLE 7

| Cervical Samples | | |
|---|---|---|
| Cytological Diagnosis: | | 10 HSIL |
| Immuno-Cytological Evaluation | | |
| $p16^{INK4a}$ | pos. | 10 |
| | neg. | 0 |
| $p14^{ARF}$ | pos. | 8 |
| | neg. | 2 |
| Her-2/Neu | pos. | 2 |
| | neg. | 8 |
| ELISA Evaluation | | |
| $p16^{INK4a}$ | pos. | 10 |
| | neg. | 0 |
| $p14^{ARF}$ | pos. | 9 |
| | neg. | 1 |
| Her-2/Neu | pos. | 3 |
| | neg. | 7 |
| Bladder Samples | | |
| Cytological Diagnosis: | | 10 Carcinomas |
| Immuno-Cytological Evaluation | | |
| $p16^{INK4a}$ | pos. | 0 |
| | neg. | 10 |
| $p14^{ARF}$ | pos. | 1 |
| | neg. | 9 |
| Her-2/Neu | pos. | 6 |
| | neg. | 4 |
| ELISA Evaluation | | |
| $p16^{INK4a}$ | pos. | 0 |
| | neg. | 10 |
| $p14^{ARF}$ | pos. | 0 |
| | neg. | 10 |
| Her-2/Neu | pos. | 5 |
| | neg. | 5 |
| DCIS Samples | | |
| Cytological Diagnosis: | | 10 DCIS |
| Immuno-Cytological Evaluation | | |
| $p16^{INK4a}$ | pos. | 0 |
| | neg. | 10 |
| $p14^{ARF}$ | pos. | 0 |
| | neg. | 10 |
| Her-2/Neu | pos. | 6 |
| | neg. | 4 |
| ELISA Evaluation | | |
| $p16^{INK4a}$ | pos. | 0 |
| | neg. | 10 |
| $p14^{ARF}$ | pos. | 1 |
| | neg. | 9 |
| Her-2/Neu | pos. | 7 |
| | neg. | 3 |

It turned out that for $p16^{INK4a}$ in 100% of the tested cases there was good correlation between the cytologically assessed $p16^{INK4a}$ staining pattern and $p16^{INK4a}$ positivity in an ELISA testing format using solubilized preservCyt™ samples for the analysis. For $p14^{ARF}$ the correlation was 93%. For Her-2/Neu a correlation of more than 90% between the immuno-cytochemical detection of the overexpression and the positivity in the ELISA format could be detected.

The results of the above examples show that the biochemical testing format using solubilized LBC samples may be applied on the same specimens as the immuno-cytochemical analysis. As the biochemical testing consumes only a fraction of the LBC sample it may easily applied as an adjunct to the immuno-cytochemical analysis.

There is good correlation between the immuno-cytochemical results and the ELISA results. This shows that the method according to the present invention is suited to assess diagnosis in various kinds of medically relevant conditions where liquid based cytology is currently applied either as ajunct or conjunct testing or as the case may be as a stand alone diagnostic test.

Example 6

Immunochemical and RT-PCR Analysis of mRNA/protein Levels of MCM-5 and MCM-2 in Liquid Based Cytology Samples from Urine 20 LBC samples of urine cells in CytoLyt™ were used for the present example. RT-PCR was performed in the same way as given in Example 3. Protein analysis was performed in a strip test formula as given in Example 2 and in parallel in an ELISA format as given in Example 1. Experimental procedures were performed as given in these examples.

It could be shown that MCM-5 may easyliy be detected in lysates from urine LBC samples. The results obtained by the biochemical non-cell based assay on the protein as well as on the nucleic acid level corresponds pretty good to the results obtained from cytology. In cytology immuno-cytological staining for MCM-5 protein was used as aid in assessment of diagnosis.

The invention, and the manner and process of making and using it, are now described in such, full, clear, concise and exact terms as to enable any person skilled in the art to which it pertains, to make and use the same. It is to be understood that the foregoing describes preferred embodiments of the present invention and that modifications may be made therein without departing from the scope of the present invention as set froth in the claims. To particularly point and distinctly claim the subject matter regarded as invention, the following claims conclude this specification.

We claim:

1. A method for detecting neoplastic disorders from a solubilized body sample of a human subject, the method comprises the steps of:
   (a) obtaining a liquid-based cytological (LBC) body sample in a preservative solution comprising an alcohol and metal ions from a human subject,
   (b) solubilizing the body sample in a lysis medium, and
   (c) determining the overexpression of a marker molecule selected from the group consisting of:
      i) a cyclin dependent kinase inhibitor selected from the group consisting of $p16^{INK4a}$, p13.5, p14, $p15^{INK4b}$, $p18^{INK4c}$, $p19^{INK4d}$, $p21^{WAF1/CIP1}$, and $p27^{KIP1}$; and
      ii) the cell cycle regulatory protein $p14^{ARF}$;
   in the solubilized body sample by comparing the level of the marker molecule within said solubilized body sample with the level of the marker molecule present in a solubilized healthy human body sample.

2. The method according to claim 1, wherein the marker molecule is $p16^{INK4a}$.

3. The method according to claim 1, wherein the neoplastic disorders are selected from the group consisting of i) cervical cancer or a precursor lesion thereof; ii) cancer of the respiratory tract or a precursor lesion thereof; iii) cancer of the urinary system or a precursor lesion thereof; iv) cancer associated with HPV infection or a precursor lesion thereof; v) cancer of the reproductive tract or a precursor lesion thereof; and vi) cancer of the anogenital tract or a precursor lesion thereof.

4. The method according to claim 1, wherein the body sample of a human subject is solubilized
   a. immediately after obtaining the sample,
   b. after storage and/or transport in a storage buffer, or
   c. after transport in a transportation buffer.

5. The method according to claim 1, wherein the levels of two or more said marker molecules are determined.

6. The method according to claim 1, wherein the detection of the marker molecules is performed using at least one probe specifically for the marker molecules.

7. The method according to claim 6, wherein the probe is detectably labeled.

8. The method according to claim 7, wherein the label is selected from the group consisting of a radioisotope, a bioluminescent compound, a chemiluminescent compound, an electroluminescent compound, a fluorescent compound, a metal chelate, an enzyme, and a biologically relevant binding structure.

9. The method according to claim 6, wherein the probe is a protein.

10. The method according to claim 9, wherein the probe is an antibody, an antibody fragment, a miniantibody, or a peptidomimetic comprising an antigen binding epitope.

11. The method according to claim 1, wherein the level of the marker molecule in the healthy human body sample is provided as a predetermined value to set up a threshold for the detection procedure.

12. The method according to claim 1, wherein the level of the marker molecule in a healthy human body sample is determined from a standardized sample solution, or from a representative number of healthy human body samples.

13. The method according to claim 1, wherein the determination of the marker molecule in a healthy human body sample is carried out:
   a. in the course of the detection procedure,
   b. in the course of calibration of the detection system,
   c. once for each lot of detection reagents, or
   d. as a standard value for the detection method.

14. The method according to claim 1, wherein the lysis medium comprises at least one composition selected from the group consisting of chaotropic agents, anionic detergents, cationic detergents, non-ionic detergents, amphoteric detergents, and alkaline compositions.

15. The method according to claim 1, wherein the lysis medium comprises at least one composition selected from the group consisting of a proteinase inhibitor, a DNAse inhibitor, and an RNAse inhibitor.

16. The method according to claim 15, wherein the proteinase inhibitor is selected from the group consisting of inhibitors to serine proteinases, inhibitors to cysteine proteinases, inhibitors to aspartic proteinases, inhibitors to metallo proteinases, inhibitors to acidic proteinases, inhibitors to neutral proteinases, and inhibitors to alkaline proteinases.

17. The method according to 1, wherein the lysis medium comprises at least one non-ionic detergent and at least one proteinase inhibitor.

18. The method according to claim 17, wherein the lysis medium contains Triton X-100 and at least one inhibitor of serine proteinases.

19. A method for assessing diagnosis of medically relevant conditions from a solubilized LBC sample comprising
  a. obtaining a LBC body sample in a preservative solution comprising an alcohol and metal ions from a human subject,
  b. solubilizing the body sample in a lysis medium,
  c. detecting the presence or absence and/or the level of a marker molecule characteristic for a medically relevant condition on the protein, peptide, or nucleic acid level in the solubilized body sample;
  d. comparing the presence or absence and/or the level of said marker molecule in the solubilized LBC sample to the presence or absence and/or the level of said marker molecule known to be characteristic for a healthy non-diseased body sample; and
  e. assessing diagnosis on the medically relevant condition based on the comparison of d.

20. The method according to claim 19, wherein the assessment of diagnosis is based on one feature selected from the group consisting of:
  a. the presence or absence of the marker molecule, wherein the presence or absence of the marker molecule is characteristic for a diseased sample;
  b. the marker molecule is overexpressed in the cells contained in the LBC sample compared to a healthy non-diseased body sample;
  c. expression of the marker molecule is lowered or lost in comparison to the expression present in a healthy non-diseased body sample; and
  d. a modified form of the marker molecule is expressed in the cells present in the LBC sample compared to the marker molecule present in healthy non-diseased body samples.

21. The method according to claim 19, wherein the medically relevant condition is a disease.

22. The method according to claim 21, wherein the disease is a cell proliferative disorder, cancer or a precursor lesion.

23. The method according to claim 22, wherein the cancer is cancer of the head and the neck, cancer of the respiratory tract, cancer of the gastrointestinal tract, cancer of the skin and its appendages, cancer of the central and peripheral nervous system, cancer of the urinary system, cancer of the reproductive system, anogenital cancer, cancer of the endocrine system, cancer of the soft tissues and bone, or cancer of the lymphopoietic and hematopoietic system.

24. The method of claim 23, wherein the anogenital cancer is cervical cancer.

25. The method according to claim 19, wherein the marker molecules are selected from the group consisting of cell cycle regulatory proteins, metalloproteinases, transmembrane proteins, calcium binding proteins, growth factors, marker molecules characteristic for viral infections, cell proliferation markers, markers associated with DNA replication, tumor marker proteins, and the nucleic acids coding for the respective proteins.

26. The method of claim 25, wherein the tumor marker proteins are selected from the group consisting of cyclin-dependent kinase inhibitors, p53, pRb, p14ARF, cyclin E, cyclin A, cyclin B, MN, her2/neu, mdm-2, bcl-2, claudin 1, EGF-Receptor, MCM2, MCM3, MCM4, MCM5, MCM6, MCM7, CDC2, CDC6, CDC7 protein kinase, CDC14 protein phosphatase, Dbf4, PCNA, Ki67, KiS1, Id1, osteopontin, CD46, GRP, renal dipeptidase, and TGFβII receptor.

27. The method according to claim 26, wherein the cyclin-dependent kinase inhibitor is $p16^{INK4a}$.

28. The method according to claim 26, wherein the cyclin-dependent kinase inhibitor is selected from the group consisting of p13.5, p14, $p15^{INK4b}$, $p18^{INK4c}$, $p19^{INK4d}$, $p21^{WAF1/CIP1}$, and $p27^{KIP1}$.

29. The method according to claim 25, wherein the marker molecules characteristic for viral infections are viral proteins.

30. The method according to claim 29 wherein the viral protein is a HPV protein derived from a HPV gene selected from the group consisting of HPV L1, HPV L2, HPV E1, HPV E2, HPV E4, HPV E5, HPV E6 and HPV E7.

31. The method according to claim 19, wherein the detection of the marker molecules is performed using at least one probe specifically for the molecules to be detected.

32. The method according to claim 31, wherein the probe is detectably labeled.

33. The method according to claim 32, wherein the label is selected from the group consisting of a radioisotope, a bioluminescent compound, a chemiluminescent compound, an electroluminescent compound, a fluorescent compound, a metal chelate, an enzyme, or a biologically relevant binding structure.

34. The method according to claim 31, wherein the probe is an antibody, an antibody fragment, a miniantibody, a peptidomimetic comprising an antigen binding epitope, or a nucleic acid complementary or reverse complementary to the marker molecule.

35. The method according to claim 19, wherein the amount of the LBC sample for application in the method is normalized with respect to information obtained from cytological specimens prepared from the LBC sample.

* * * * *